US012635866B2

(12) United States Patent
Fuentes-Ortega et al.

(10) Patent No.: US 12,635,866 B2
(45) Date of Patent: May 26, 2026

(54) DILATION INSTRUMENT WITH MALLEABLE GUIDE

(71) Applicants: Acclarent, Inc., Irvine, CA (US);
Biosense Webster (Israel) Ltd.,
Yokneam (IL)

(72) Inventors: Cesar Fuentes-Ortega, Pasadena, CA
(US); Henry F. Salazar, Pico Rivera,
CA (US); Raymond Yue-sing Tang,
Rosemead, CA (US); Shubhayu Basu,
Anaheim, CA (US); Kokou A. Amefia,
Aliso Viejo, CA (US); **Erica E.
Lovejoy**, La Puente, CA (US);
Brittanie Chu, Chino Hills, CA (US)

(73) Assignees: Acclarent, Inc., Irvine, CA (US);
Biosense Webster (Israel) Ltd.,
Yokneam (IL)

( * ) Notice: Subject to any disclaimer, the term of this
patent is extended or adjusted under 35
U.S.C. 154(b) by 110 days.

(21) Appl. No.: 18/539,855

(22) Filed: Dec. 14, 2023

(65) Prior Publication Data

US 2024/0285158 A1      Aug. 29, 2024

Related U.S. Application Data

(60) Provisional application No. 63/447,976, filed on Feb.
24, 2023.

(51) Int. Cl.
*A61B 1/07*          (2006.01)
*A61B 1/233*         (2006.01)
(Continued)

(52) U.S. Cl.
CPC ................ *A61B 1/07* (2013.01); *A61B 1/233*
(2013.01); *A61B 17/00* (2013.01); *A61M*
*25/09* (2013.01);
(Continued)

(58) Field of Classification Search
CPC ........... A61B 1/07; A61B 1/233; A61B 17/00;
A61B 2017/00946; A61B 17/24;
(Continued)

(56) References Cited

U.S. PATENT DOCUMENTS 7,720,521 B2      5/2010  Chang et al.
8,282,667 B2     10/2012  Drontle et al.
(Continued)

FOREIGN PATENT DOCUMENTS

EP           3735898 A1     11/2020

OTHER PUBLICATIONS

Partial European Search Report in co-pending EP Application No.
24159269.0, 16 pages.

*Primary Examiner* — Richard G Louis
(74) *Attorney, Agent, or Firm* — Barnes & Thornburg
LLP

(57) ABSTRACT

An apparatus includes a body and a shaft assembly extending distally from the body. The shaft assembly includes a malleable distal portion and an enlarged tip positioned at a distal end of the malleable distal portion. The shaft assembly further includes a position sensor positioned within the enlarged tip. The position sensor is configured to generate a signal indicating a position of the enlarged tip in three-dimensional space. The shaft assembly further includes an illuminating element positioned within the enlarged tip. The illuminating element is configured to emit light. The shaft assembly further includes an inflatable balloon positioned proximal to the enlarged tip. The inflatable balloon is configured to dilate a passageway in an ear, nose, or throat of a patient.

18 Claims, 17 Drawing Sheets

(51) Int. Cl.
    *A61B 17/00*       (2006.01)
    *A61M 25/09*     (2006.01)

(52) U.S. Cl.
    CPC .............. *A61B 2017/00946* (2013.01); *A61M 2025/09008* (2013.01); *A61M 2025/09116* (2013.01)

(58) Field of Classification Search
    CPC ........ A61M 25/09; A61M 2025/09008; A61M 2025/09116; A61M 25/0136; A61M 29/02; A61M 25/0113
    See application file for complete search history.

(56)            References Cited

U.S. PATENT DOCUMENTS

| | | | |
|---|---|---|---|
| 8,834,513 B2 | 9/2014 | Hanson et al. | |
| 9,155,492 B2 | 10/2015 | Jenkins et al. | |
| 9,192,748 B2 | 11/2015 | Ressemann et al. | |
| 9,579,448 B2 | 2/2017 | Chow et al. | |
| 9,757,018 B2 | 9/2017 | Kesten et al. | |
| 9,820,688 B2 | 11/2017 | Jenkins et al. | |
| 9,974,617 B2 | 5/2018 | Flexman et al. | |
| 10,137,285 B2 | 11/2018 | Jenkins et al. | |
| 10,206,821 B2 | 2/2019 | Campbell et al. | |
| 10,271,719 B2 | 4/2019 | Morriss et al. | |
| 10,307,519 B2 | 6/2019 | Drontle et al. | |
| 10,350,011 B2 | 7/2019 | Flexman et al. | |
| 10,463,242 B2 | 11/2019 | Kesten et al. | |
| 10,561,370 B2 | 2/2020 | Salazar et al. | |
| 10,772,489 B2 | 9/2020 | Govari et al. | |
| 10,864,046 B2 | 12/2020 | Salazar et al. | |
| 11,013,896 B2 | 5/2021 | Chan et al. | |
| 11,065,061 B2 | 7/2021 | Makower | |
| 11,103,249 B2 | 8/2021 | Zoabi et al. | |
| 11,419,623 B2 | 8/2022 | Palushi et al. | |
| 11,534,192 B2 | 12/2022 | Goldfarb et al. | |
| 2006/0004286 A1* | 1/2006 | Chang | A61B 90/16 |
| | | | 606/198 |
| 2009/0076446 A1 | 3/2009 | Dubuclet, IV et al. | |
| 2009/0088728 A1 | 4/2009 | Dollar et al. | |
| 2012/0253123 A1* | 10/2012 | Shimizu | A61B 1/00082 |
| | | | 600/116 |
| 2016/0310041 A1 | 10/2016 | Jenkins et al. | |
| 2018/0110938 A1* | 4/2018 | Trzecieski | A61L 9/00 |
| 2018/0280046 A1 | 10/2018 | Ngo-Chu et al. | |
| 2019/0091450 A1 | 3/2019 | Chandler et al. | |
| 2019/0175889 A1 | 6/2019 | Ressemann et al. | |
| 2019/0374755 A1* | 12/2019 | Palushi | A61B 17/3415 |
| 2019/0388156 A1 | 12/2019 | Shameli | |
| 2021/0361912 A1 | 11/2021 | Matlock et al. | |
| 2022/0113204 A1 | 4/2022 | Hayes | |

* cited by examiner

342

344

346

340

DILATION INSTRUMENT WITH MALLEABLE GUIDE

PRIORITY

This application claims priority to U.S. Provisional Pat. App. No. 63/447,976, entitled "Dilation Instrument with Malleable Guide," filed Feb. 24, 2023, the disclosure of which is incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. No. 11,534,192, entitled "Methods and Apparatus for Treating Disorders of the Sinuses," issued Dec. 27, 2022, the disclosure of which is incorporated by reference herein, in its entirety; U.S. Pat. No. 9,579,448, entitled "Balloon Dilation Catheter System for Treatment and Irrigation of the Sinuses," issued Feb. 28, 2017, the disclosure of which is incorporated by reference herein, in its entirety; U.S. Pat. No. 9,155,492, entitled "Sinus Illumination Lightwire Device," issued Oct. 13, 2015, the disclosure of which is incorporated by reference herein, in its entirety; and U.S. Pub. No. 2021/0361912, entitled "Shaft Deflection Control Assembly for ENT Guide Instrument," published Nov. 25, 2021, the disclosure of which is incorporated by reference herein, in its entirety.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Pat. No. 10,206,821, entitled "Eustachian Tube Dilation Balloon with Ventilation Path," issued Feb. 19, 2019, the disclosure of which is incorporated by reference herein, in its entirety; and U.S. Pat. No. 11,013,896, entitled "Method and System for Eustachian Tube Dilation," issued May 25, 2021, the disclosure of which is incorporated by reference herein, in its entirety.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
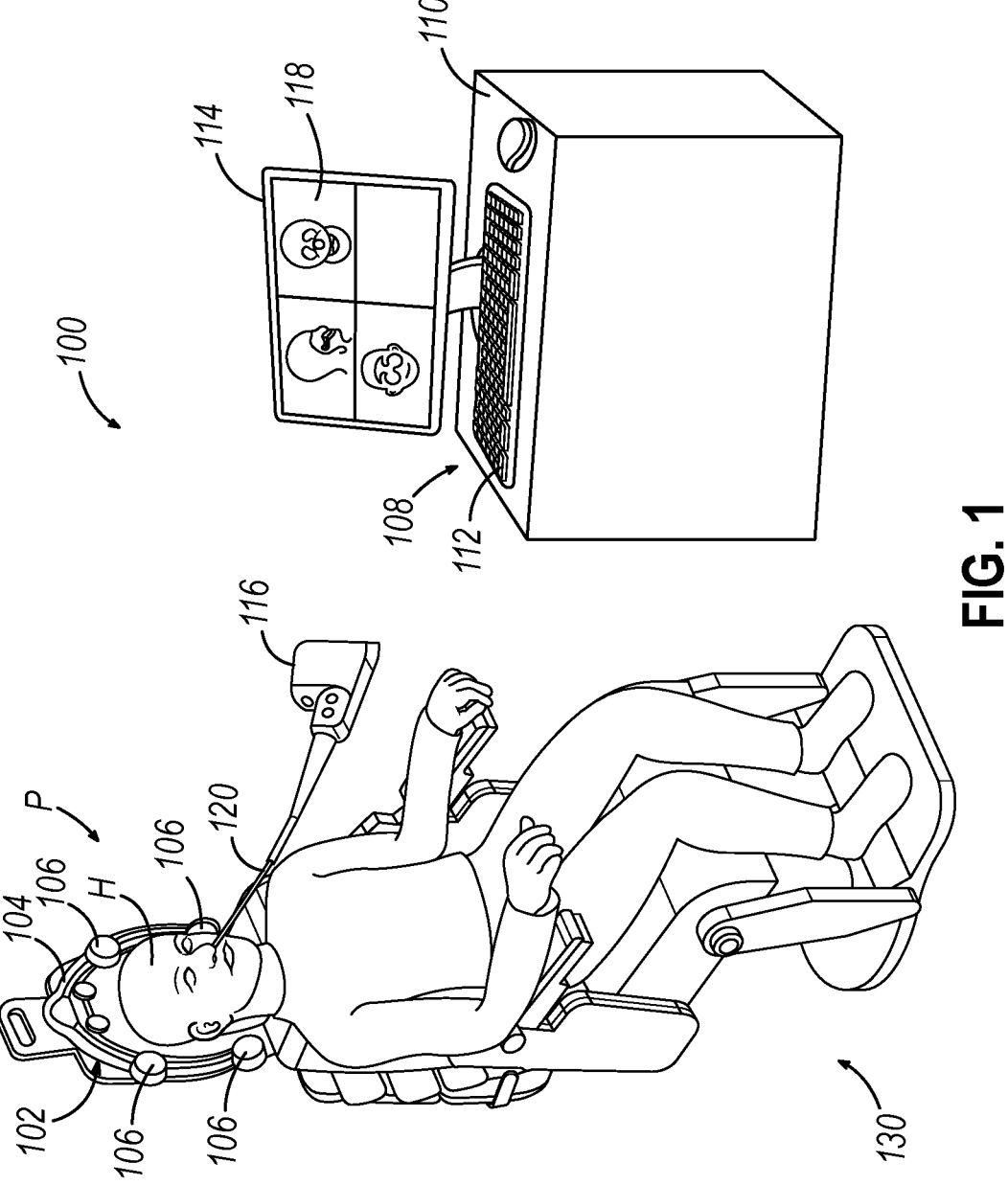
FIG. 1 depicts a schematic perspective view of an example of a surgical navigation system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

As used herein, the terms "about" and "approximately" for any numerical values or ranges are intended to encompass the exact value(s) referenced as well as a suitable dimensional tolerance that allows the part or collection of components to function for its intended purpose as described herein.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Example of an Image Guided Surgery Navigation System

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an example of a IGS navigation system (100) enabling an ENT procedure to be performed using image guidance. In addition to or in lieu of having the components and operability described herein IGS navigation system (100) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and U.S. Pat. No. 11,065,061, entitled "Systems and Methods for Performing Image Guided Procedures within the Ear, Nose, Throat and Paranasal Sinuses," issued Jul. 20, 2021, the disclosure of which is incorporated by reference herein, in its entirety.

IGS navigation system (100) of the present example comprises a field generator assembly (102), which comprises magnetic field generators (106) that are integrated into a horseshoe-shaped frame (104). Field generators (106) are operable to generate alternating magnetic fields of different frequencies around the head (H) of the patient (P). A navigation guidewire (120) is inserted into the head (H) of the patient (P) in this example. Navigation guidewire (120) may be a standalone device or may be positioned on an end effector or other location of a medical instrument such as a surgical cutting instrument or dilation instrument. In the present example, frame (104) is mounted to a chair (130), with the patient (P) being seated in the chair (130) such that frame (104) is located adjacent to the head (H) of the patient (P). By way of example only, chair (130) and/or field generator assembly (102) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein, in its entirety.

IGS navigation system (100) of the present example further comprises a processor (108), which controls field generators (106) and other elements of IGS navigation system (100). For instance, processor (108) is operable to drive field generators (106) to generate alternating electromagnetic fields; and process signals from navigation guidewire (120) to determine the location of a sensor in navigation guidewire (120) within the head (H) of the patient (P). Processor (108) comprises a processing unit communicating with one or more memories. Processor (108) may further include a central processing unit (CPU) of a computer system, a microprocessor, an application-specific integrated circuit (ASIC), other kinds of hardware components, and combinations thereof. Processor (108) of the present example is mounted in a console (110), which comprises operating controls (112) that include a keypad and/or a pointing device such as a mouse or trackball. A physician uses operating controls (112) to interact with processor (108) while performing the surgical procedure.

Navigation guidewire (120) includes a sensor (not shown) that is responsive to positioning within the alternating magnetic fields generated by field generators (106). A coupling unit (116) is secured to the proximal end of navigation guidewire (120) and is configured to provide communication of data and other signals between console (110) and navigation guidewire (120). Coupling unit (116) may provide wired or wireless communication of data and other signals between console (110) and navigation guidewire (120).

In the present example, the sensor of navigation guidewire (120) comprises at least one electrically conductive coil at the distal end of navigation guidewire (120). When such a coil is positioned within an alternating electromagnetic field generated by field generators (106), the alternating magnetic field may generate electrical current in the coil, and this electrical current may be communicated proximally along the electrical conduit(s) in navigation guidewire (120) and further to processor (108) via coupling unit (116). This phenomenon may enable IGS navigation system (100) to determine the location of the distal end of navigation guidewire (120) or other medical instrument (e.g., dilation instrument, surgical cutting instrument, etc.) within a three-dimensional space (i.e., within the head (H) of the patient (P), etc.). To accomplish this, processor (108) executes an algorithm to calculate location coordinates of the distal end of navigation guidewire (120) from the position related signals of the coil(s) in navigation guidewire (120). While the position sensor is located in guidewire (120) in this example, such a position sensor may be integrated into various other kinds of instruments, including those described in greater detail below.

Processor (108) uses software stored in a memory of processor (108) to calibrate and operate IGS navigation system (100). Such operation includes driving field generators (106), processing data from navigation guidewire (120), processing data from operating controls (112), and a driving display screen (114). In some implementations, operation may also include monitoring and enforcement of one or more safety features or functions of IGS navigation system (100). Processor (108) is further operable to provide video in real time via display screen (114), showing the position of the distal end of navigation guidewire (120) in relation to a video camera image of the patient's head (H), a CT scan image of the patient's head (H), and/or a computer generated three-dimensional model of the anatomy within and adjacent to the patient's nasal cavity. Display screen (114) may display such images (118) simultaneously and/or superimposed on each other during the surgical procedure. Such displayed images (118) may also include graphical representations of instruments that are inserted in the patient's head (H), such as navigation guidewire (120), such that the operator may view the virtual rendering of the instrument at its actual location in real time. By way of example only, display screen (114) may provide images (118) in accordance with at least some of the teachings of U.S. Pat. No. 10,463,242, entitled "Guidewire Navigation for Sinuplasty," issued Nov. 5, 2019, the disclosure of which is incorporated by reference herein, in its entirety. In the event that the operator is also using an endoscope, the endoscopic image may also be provided on display screen (114).

The images (118) provided through display screen (114) may help guide the operator in maneuvering and otherwise manipulating instruments within the patient's head (H) when such instruments incorporate navigation guidewire (120). It should also be understood that other components of a surgical instrument and other kinds of surgical instruments, as described below, may incorporate a sensor like the sensor of navigation guidewire (120).

II. Example of a Dilation Instrument with One Slider and Fixed Ball Tip

Figure 2A:
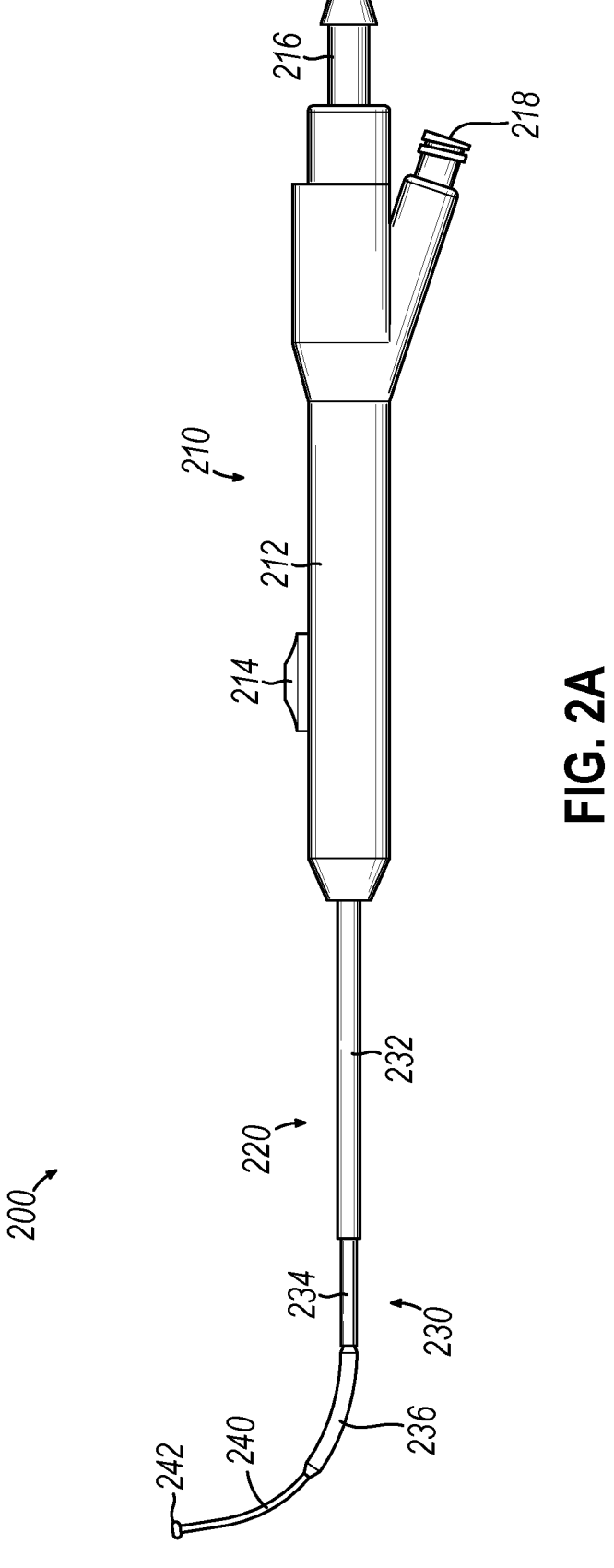
FIG. 2A depicts a side elevational view of an example of a dilation instrument, with a dilation catheter in a proximal position, and with a balloon of the dilation catheter in a deflated state.
Figure 2B:
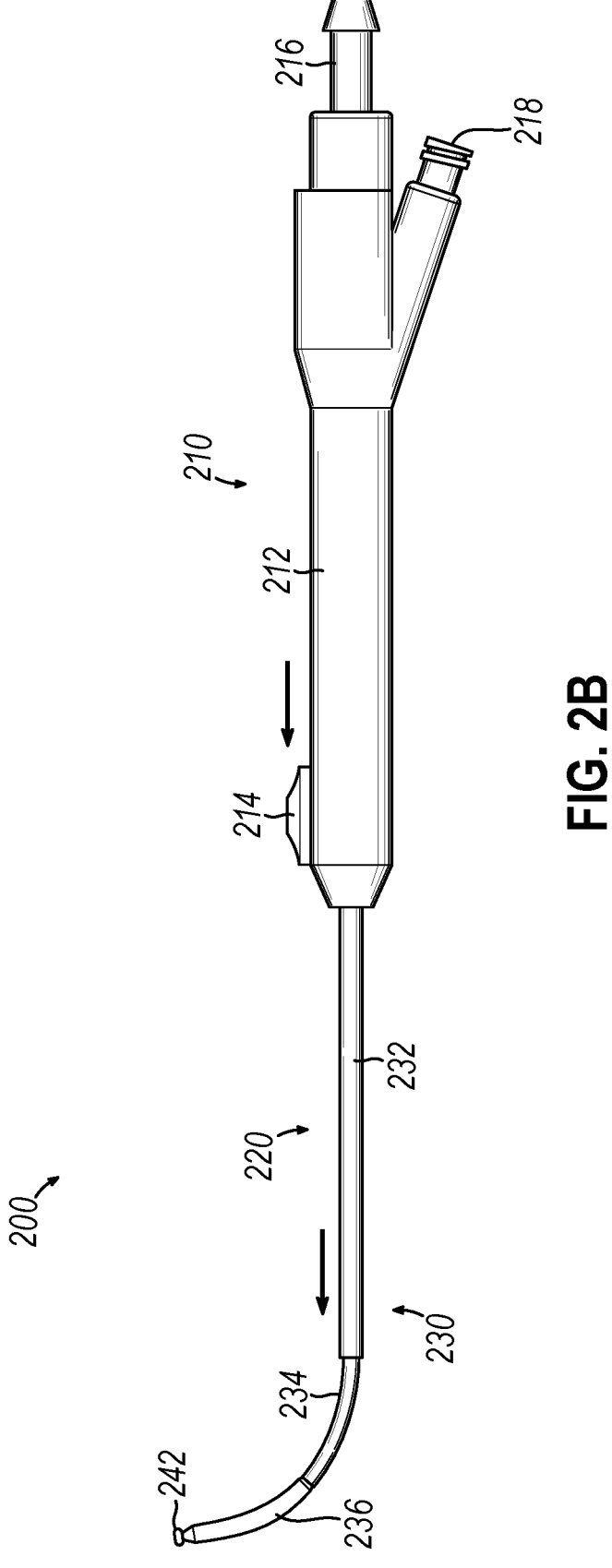
FIG. 2B depicts a side elevational view of the dilation instrument of FIG. 2A, with the dilation catheter in a distal position, and with the balloon in the deflated state.
Figure 2C:
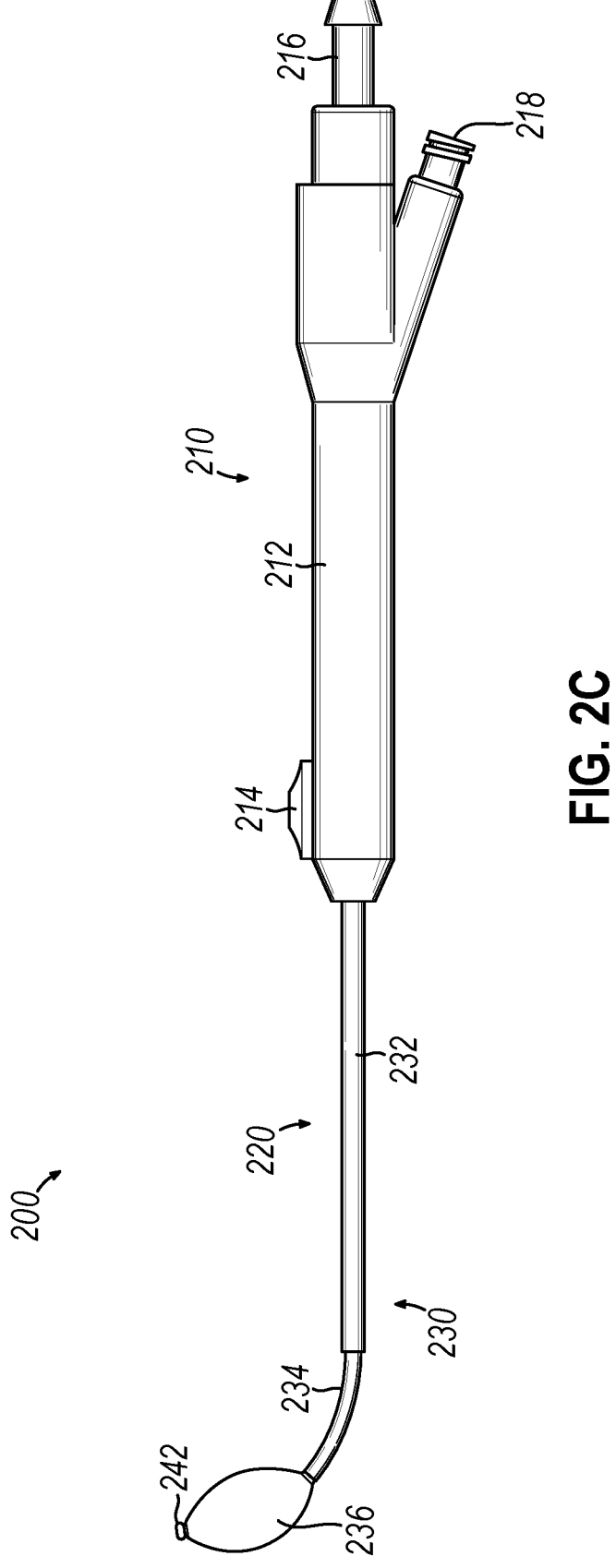
FIG. 2C depicts a side elevational view of the dilation instrument of FIG. 2A, with the dilation catheter in the distal position, and with the balloon in an inflated state.

FIGS. 2A-2C show an example of a dilation instrument (200) that may be used to dilate the ostium or other drainage passageway of a paranasal sinus, to dilate a Eustachian tube, or to dilate some other anatomical passageway (e.g., within the ear, nose, or throat, etc.). By way of example only, dilation instrument (200) may be configured and operable in accordance with at least some of the teachings of any of the patent references cited herein. Dilation instrument (200) of the present example comprises a handle assembly (210) and a shaft assembly (220). Handle assembly (210) includes a body (212) that may be grasped and operated by a single hand of an operator. A pair of ports (216, 218) extend proximally from body (212); while shaft assembly (220) extends distally from body (212). A slider (214) is slidably positioned along body (212) and is operable to drive translation of a dilation catheter (230) relative to body (212) as will be described in greater detail below.

Shaft assembly (220) includes dilation catheter (230) and a malleable guide member (240). Dilation catheter (230) includes a rigid proximal portion (230) and a flexible distal portion (234). Rigid proximal portion (230) is fixedly secured relative to slider (214). In some versions, proximal portion (230) comprises a metallic hypotube while distal portion (234) comprises a polymeric material. An inflatable balloon (236) is integrated into distal portion (234). Balloon (236) is fluidically coupled with port (218), such that an inflation fluid (e.g., saline, etc.) may be communicated to or from port (218) to selectively inflate or deflate balloon (236), respectively. In some versions, balloon (236) comprises a non-extensible material; while in other versions, balloon (236) comprises an extensible material. Balloon (236) is configured such that, in a deflated state (FIGS. 2A-2B), balloon (236) may be slidably positioned in a paranasal sinus ostium, another drainage passageway of a paranasal sinus, a Eustachian tube, or some other anatomical passageway. Balloon (236) is further configured such that, in an inflated state (FIG. 2C), balloon (236) will dilate the opening or other passageway in which balloon (236) is disposed.

Guide member (240) of the present example is in the form of a rail, with dilation catheter (230) being slidably disposed about the exterior of malleable guide member (240). The outer diameter of guide member (240) is thus smaller than the inner diameter of dilation catheter (230). Guide member (240) is malleable such that guide member (240) may be manually bent to achieve a desired bend angle; and maintain that bend angle as guide member (240) is inserted through a nasal cavity (or other access site) to reach a targeted anatomical opening or other anatomical passageway. Guide member (240) thus has sufficient flexibility to bend to form a desired bend angle; while having sufficient rigidity to maintain the desired bend angle during a dilation procedure. Use of instrument (200) in a dilation procedure will thus not cause guide member (240) to undesirably unbend or rebend. By way of example only, guide member (240) may comprise a metallic hypotube. In the present example, the proximal portion of guide member (240) is fixedly secured relative to body (212) of handle assembly (210).

Guide member (240) of the present example further includes an enlarged tip in the form of a ball tip (242). In some versions, ball tip (242) is substantially spherical. In some other versions, ball tip (242) has a shape similar to that of a blueberry. Alternatively, ball tip (242) may have any other suitable configuration. In the present example, ball tip (242) is small enough to allow ball tip (242) to traverse a paranasal sinus ostium, another drainage passageway of a paranasal sinus, or a Eustachian tube; yet is large enough to prevent ball tip (242) from traversing an isthmus between a Eustachian tube and a middle ear region of a patient. In some other variations, ball tip (242) is omitted. In some such variations, the distal tip of guide member (240) is still atraumatic but is not enlarged.

In some versions, one or more electrically powered components (e.g., LED, position sensor, etc.) may be positioned in ball tip (242); and port (216) may provide a corresponding coupling between instrument (200) and an external power source. An example of how such components may be integrated into ball tip (242) will be described in greater detail below with reference to FIG. 3. In addition, or in the alternative, guide member (240) may include an internal lumen; and ball tip (242) may include a corresponding opening. In some such versions, a guidewire or other instrument may be inserted via port (216) and be positioned in the lumen of guide member (240); and may further pass through the opening of ball tip (242). An example of such an arrangement is described in greater detail below with reference to FIGS. 4A-4B. In addition, or in the alternative, port (216) may be used to communicate suction, irrigation fluid, therapeutic fluid, and or other fluid through a lumen of guide member (240) and opening of ball tip (242). Alternatively, port (216) may be used in any other suitable fashion; or may be simply omitted.

In an example of a use of instrument (200), the operator may form a desired bend in guide member (240) before inserting guide member (240) into the patient. This bending step may be performed while slider (214) and dilation catheter (230) are proximally positioned as shown in FIG. 2A. As shown in FIG. 2A, the entirety of distal portion (234), and a substantial portion of proximal portion (232) are exposed when dilation catheter (230) is in the proximal position in this example. As also shown in FIG. 2A, a portion of guide member (240) is exposed relative to dilation catheter (230) when dilation catheter (230) is in the proximal position in this example. It should be understood that the bend angle shown in FIG. 2A is just one example. In some scenarios, the bend angle may be more acute or more obtuse than the bend angle shown in FIG. 2A. Moreover, guide member (240) may be left substantially straight in some examples. In any case, the bend angle may be chosen based on the location and access path of the targeted anatomical opening or other anatomical passageway.

After the desired bend angle has been formed in guide member (240) the operator may insert shaft assembly (220) into the nasal cavity or other access passageway; and further insert guide member (240) into the targeted anatomical opening or other anatomical passageway. This insertion may be performed while dilation catheter (230) remains in the proximal position as shown in FIG. 2A. After guide member (240) has suitably traversed the targeted anatomical opening or other anatomical passageway, the operator may hold body (212) stationary while advancing slider (214) distally, thereby advancing dilation catheter (230) along guide member (240) until slider (214) and dilation catheter (230) reach a distal position as shown in FIG. 2B. As dilation catheter (230) advances to this distal position, dilation catheter (230) may advance into the targeted anatomical opening or other anatomical passageway, such that balloon (236) may be positioned the targeted anatomical opening or other anatomical passageway. It should be understood that balloon (236) may remain in the deflated state during this positioning of balloon (236) in the targeted anatomical opening or other anatomical passageway.

After balloon (236) has been suitably positioned in the targeted anatomical opening or other anatomical passageway, balloon (236) may be inflated as shown in FIG. 2C. As noted above, such inflation may be provided by communicating fluid (e.g., saline, etc.) via port (218). The inflated balloon (236) may dilate the targeted anatomical opening or other anatomical passageway. The operator may maintain the inflated state of balloon (236) for any desired duration while balloon (236) is disposed in the targeted anatomical opening or other anatomical passageway. Balloon (236) may then be deflated. In some scenarios, the operator may repeatedly inflate and deflate balloon (236) while balloon (236) is disposed in the targeted anatomical opening or other anatomical passageway. After the targeted anatomical opening or other anatomical passageway has been sufficiently dilated by balloon (236), the operator may remove shaft assembly (220) from the patient while balloon (236) is in a deflated state. In some scenarios, the operator may bend guide member (240) again to achieve a different bend angle, then repeat the steps described above to dilate another anatomical opening or other anatomical passageway in the patient.

In addition to, or as an alternative to, the use of instrument (200) described above, instrument (200) may be used as a seeker device and/or to atraumatically move tissue within the ear, nose, or throat of the patient. For instance, guide member (240) may be bent to a desired bend angle, and ball tip (242) may be utilized to probe tissue within an anatomical cavity, to move tissue within an anatomical cavity, or to otherwise engage tissue in an anatomical cavity. This may be done before, during, and/or after a dilation procedure as described above. This may also be done even in procedures where no dilation is performed. Thus, instrument (200) may provide clinically meaningful uses even in scenarios where dilation catheter (230) is not utilized.

III. Examples of Alternative Guide Member Configurations

A. Guide Member with Integral Illuminating Feature and/or Position Sensor

Figure 3:
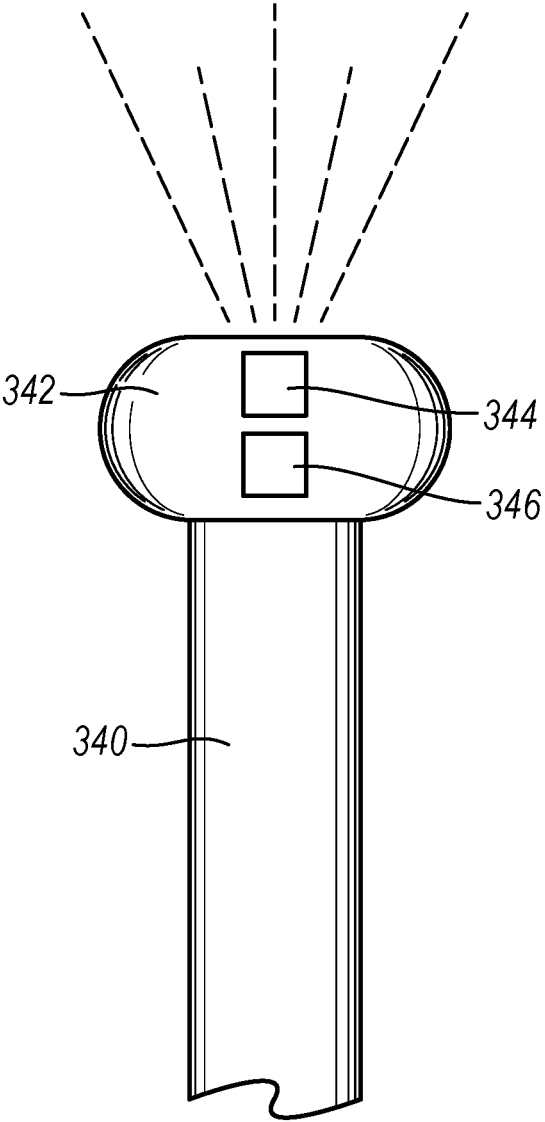
FIG. 3 depicts a schematic view of a distal portion of a guide member with an integral illuminating element and an integral position sensor.

As noted above, guide member (240) may include one or more illuminating features and/or one or more position sensors to assist the operator in positioning guide member (240) in the targeted anatomical opening or other anatomical passageway. FIG. 3 shows one example of an alternative guide member (340) that may be incorporated into instrument (200) in place of guide member (240). Guide member (340) may be configured and operable like guide member (240) except as otherwise described below. Guide member (340) of this example includes a ball tip (342) that is configured and operable just like ball tip (242) of guide member (240). However, ball tip (342) of this example includes an integral illuminating feature (344) that is operable to project light distally from ball tip (342). In some versions, illuminating feature (344) includes one or more LEDs. In such versions, one or more wires, conductive traces, or other electrically conductive elements may extend along the length of guide member (340) and into handle assembly (210). Such electrically conductive elements may be further coupled with port (216) or some other feature of handle assembly (210) to allow electrical power to be communicated to illuminating feature (344). In some variations, an electrical power source (e.g., one or more batteries) is integrated into handle assembly (210) to provide electrical power to illuminating feature (344).

In some other versions, at least a portion of ball tip (342) comprises an optically transmissive material (e.g., glass, plastic, etc.) and is in optical communication with one or more optical fibers that extend along the length of guide member (340) and into handle assembly (210). Such one or more optical fibers may be optically coupled with an external light source via port (216) or via some other coupling of handle assembly (210). Alternatively, a light source may be integrated into handle assembly (210) to provide light to illuminating feature (344) via one or more optical fibers.

Regardless of whether illuminating feature (344) includes one or more LEDs, an optically transmissive material in optical communication with one or more optical fibers, and/or some other configuration, illuminating feature (344) may facilitate positioning guide member (240) in the targeted anatomical opening or other anatomical passageway by providing transillumination. For instance, when ball tip (342) passes through a maxillary sinus ostium and enters a maxillary sinus cavity, illuminating feature (344) may provide transillumination through the cheek of the patient, thereby providing visual confirmation that guide member (340) has traversed the maxillary sinus ostium. Similarly, when ball tip (342) passes through a frontal recess and enters a frontal sinus cavity, illuminating feature (344) may provide transillumination through the forehead of the patient, thereby providing visual confirmation that guide member (340) has traversed the frontal recess.

Ball tip (342) of the present example further comprises a position sensor (346) that is configured to cooperate with an IGS navigation system (100) to thereby provide signals indicating the position of ball tip (342) in three-dimensional space. Position sensor (346) may comprise one or more coils, as described above in the context of guidewire (120) of IGS navigation system (100). One or more wires, conductive traces, or other electrically conductive elements may extend along the length of guide member (340) and into handle assembly (210). Such electrically conductive elements may be further coupled with port (216) or some other feature of handle assembly (210) to allow signals from position sensor (346) to be communicated to IGS navigation system (100). Port (216) may thus function similar to coupling unit (116) as described above. In versions of instrument (200) where guide member (340) with a position sensor (346) is used, the operator may rely on navigation system (100) to determine the real-time position of ball tip (342) in three-dimensional space, as described above in the context of tracking the position of guidewire (120), to determine when guide member (340) has reached the targeted anatomical opening or other anatomical passageway.

While ball tip (342) of the present example includes illuminating feature (344) and position sensor (346), some variations may include illuminating feature (344) and omit position sensor (346). Similarly, some variations may include position sensor (346) and omit illuminating feature (344).

Figure 4B:
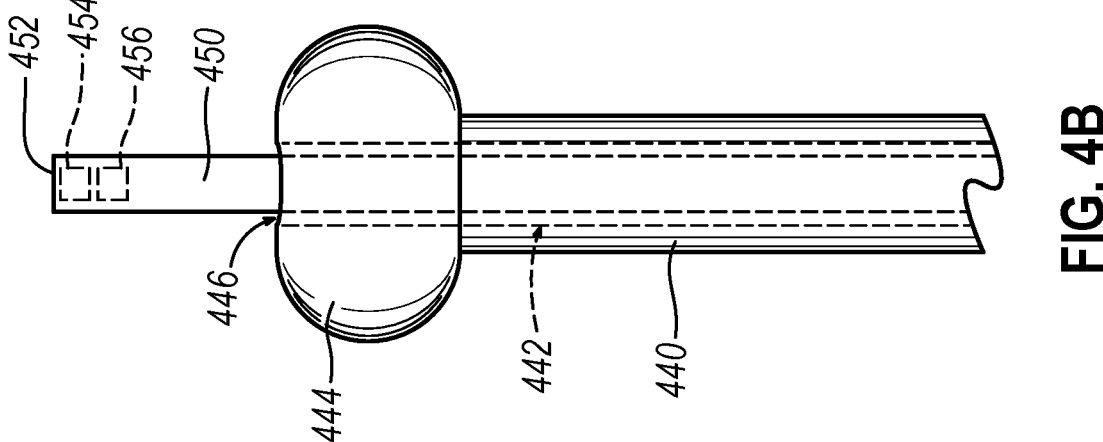
FIG. 4B depicts a schematic view of the guide member and guidewire of FIG. 4A, with the guidewire in a distal position.
Figure 4A:
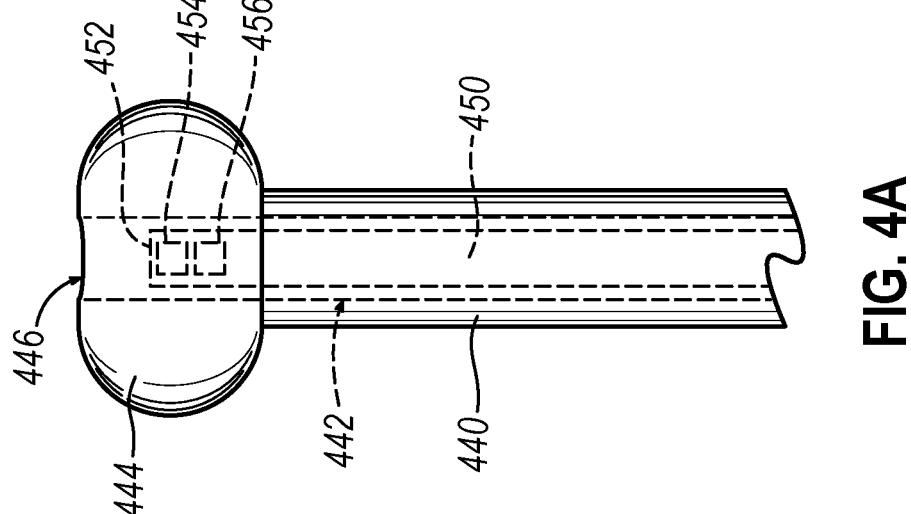
FIG. 4A depicts a schematic view of a distal portion of another guide member and a guidewire, with the guidewire in a proximal position.

B. Guide Member and Guidewire with Integral Illuminating Feature and/or Position Sensor FIGS. 4A-4B show another example of an alternative guide member (440) that may be incorporated into instrument (200) in place of guide member (240). Guide member (440) may be configured and operable like guide member (240) except as otherwise described below. Guide member (440) of this example includes a ball tip (444) that is configured and operable just like ball tip (242) of guide member (240). However, ball tip (444) of this example defines an opening (446) that communicates with a lumen (442) formed through guide member (440). A guidewire (450) is positioned in lumen (442). Guidewire (450) of this example includes an integral illuminating feature (454) and a position sensor (456) at a distal end (452) of guidewire (450). An example of how guidewire (450) may be configured to include illuminating feature (454) and position sensor (456) at distal end (452) is described in greater detail below with reference to FIGS. 5-6.

Illuminating feature (454) may facilitate positioning guidewire (450), and also guide member (440) in the targeted anatomical opening or other anatomical passageway by providing transillumination. For instance, when distal end (452) passes through a maxillary sinus ostium and enters a maxillary sinus cavity, illuminating feature (454) may provide transillumination through the cheek of the patient, thereby providing visual confirmation that guidewire (450) has traversed the maxillary sinus ostium. Similarly, when distal end (452) passes through a frontal recess and enters a frontal sinus cavity, illuminating feature (454) may provide transillumination through the forehead of the patient, thereby providing visual confirmation that guidewire (450) has traversed the frontal recess.

Position sensor (456) is configured to cooperate with an IGS navigation system (100) to thereby provide signals indicating the position of distal end (452) in three-dimensional space. Position sensor (456) may comprise one or more coils, as described above in the context of guidewire (120) of IGS navigation system (100). One or more wires, conductive traces, or other electrically conductive elements may extend along the length of guidewire (450). Such electrically conductive elements may be further coupled with a feature like coupling unit (116), to allow signals from position sensor (456) to be communicated to IGS navigation system (100). In versions of instrument (200) where guidewire (450) with a position sensor (456) is used, the operator may rely on navigation system (100) to determine the real-time position of distal end (452) in three-dimensional space, as described above in the context of tracking the position of guidewire (120), to determine when guidewire (450) has reached the targeted anatomical opening or other anatomical passageway.

While guidewire (450) of the present example includes illuminating feature (454) and position sensor (456), some variations of guidewire (450) may include illuminating feature (454) and omit position sensor (456). In some arrangements where guidewire (450) lacks position sensor (456), ball tip (444) may include an integral position sensor (346). Similarly, some variations may include position sensor (456) and omit illuminating feature (454). In some arrangements where guidewire (450) lacks illuminating feature (454), ball tip (444) may include an integral illuminating feature (344). Still other variations of guidewire (450) may omit both position sensor (456) and illuminating feature (454). In arrangements where guidewire (450) lacks both position sensor (456) and illuminating feature (454), ball tip (444) may include an integral position sensor (346) and/or an integral illuminating feature (344).

As shown in FIGS. 4A-4B, guidewire (450) may translate longitudinally relative to guide member (440) between a proximal position (FIG. 4A) and a distal position (FIG. 4B).

With guidewire (450) in the proximal position as shown in FIG. 4A, distal end (452) is recessed relative to ball tip (444). With guidewire (450) in the distal position as shown in FIG. 4B, distal end (452) is exposed distally relative to ball tip (444). By way of example only, some variations of handle assembly (210) may be modified to include an additional slider that is operable to actuate guidewire (450), to thereby transition guidewire (450) between the proximal position (FIG. 4A) and the distal position (FIG. 4B). An example of a handle assembly with an additional slider for driving a guidewire is described in greater detail below with reference to FIGS. 7A-7D. As another variation, an instrument may be configured such that longitudinal translation of a dilation catheter will drive longitudinal translation of guidewire (450) between the proximal position (FIG. 4A) and the distal position (FIG. 4B). Some examples of such an arrangement are described in U.S. Pat. No. 11,419,623, entitled "Sinuplasty Instrument with Moveable Navigation Sensor," issued Aug. 23, 2022, the disclosure of which is incorporated by reference herein, in its entirety. Another example of such an arrangement is described in greater detail below with reference to FIGS. 8A-8D.

In some other variations, guidewire (450) is not configured to translate to the distal position in FIG. 4B. In some such variations, guidewire (450) is secured relative to guide member (440) with distal end (452) being positioned at or near ball tip (444). By way of example only, guidewire (450) may be inserted via port (216); and may include a feature that selectively locks with port (216) to thereby secure the longitudinal position of guidewire (450) relative to guide member (440). In some variations where guidewire (450) is secured relative to guide member (440) with distal end (452) being positioned at or near ball tip (444), signals from position sensor (456) may effectively indicate the real-time position of ball tip (444) in three-dimensional space. In addition, or in the alternative, in some variations where guidewire (450) is secured relative to guide member (440) with distal end (452) being positioned at or near ball tip (444), light from illuminating feature (454) may project distally via opening (446) of ball tip (444).

Lumen (442) of guide member (440) may also be used for other purposes, in addition to or as an alternative to accommodating guidewire (450). For instance, lumen (442) and opening (446) may be used to communicate suction, irrigation fluid, or other fluid to a cavity or passageway within the ear, nose, or throat of a patient. In some cases, suction, irrigation fluid, or other fluid may be communicated through lumen (442) and opening (446) while guidewire (450) is disposed in lumen (442). In some other cases, guidewire (450) is removed from lumen (442) to allow suction, irrigation fluid, or other fluid may be communicated through lumen (442) and opening (446). It should also be understood that lumen (442) may be configured to slidably receive other instrumentation, such as fluid delivery needles, ablation needles, or other working instruments.

C. Guidewire with Integral Illuminating Feature and Position Sensor

Figures 5, 6:
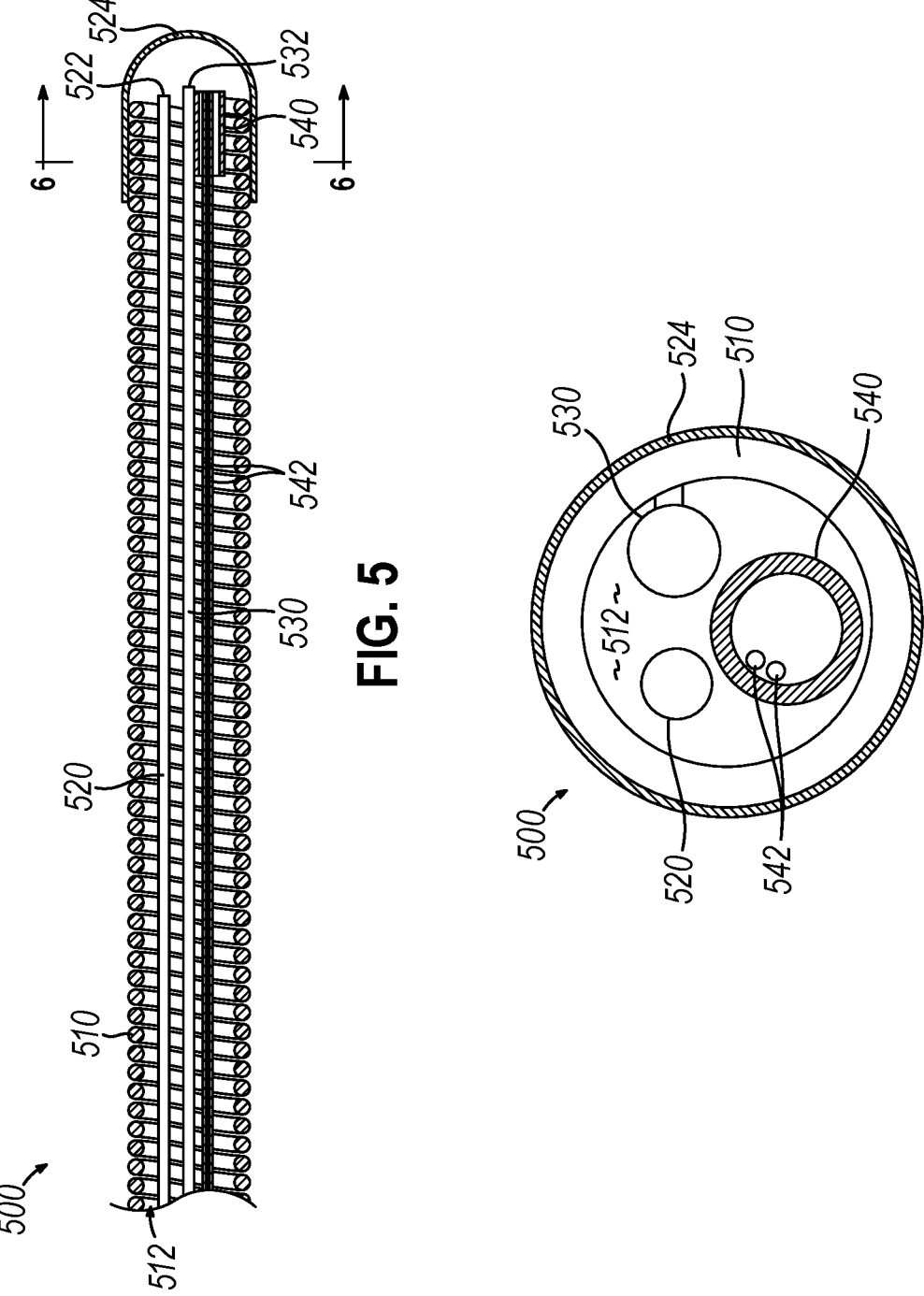
FIG. 5 depicts a cross-sectional side view of a guidewire with an integral illuminating element and an integral position sensor.
FIG. 6 depict a cross-sectional end view of the guidewire of FIG. 5, taken along line 6-6 of FIG. 5.

FIGS. 5-6 show an example of a guidewire (500) representing a form that may be taken by guidewire (450) of FIGS. 4A-4B. Guidewire (500) of this example includes an outer coil (510) that is distally coupled with a tip member (524). Outer coil (510) defines a lumen (512). An optical fiber (520), a core wire (530), and a pair of electrical wires (542) are positioned within lumen (512).

The proximal end (not shown) of optical fiber (520) may be optically coupled with a light source. Optical fiber (520) has a distal end (522) that is fixedly secured in tip member (524). Tip member (524) comprises an optically transmissive material (e.g., plastic, etc.), such that light conveyed along optical fiber (520) may be emitted through tip member (524). Optical fiber (520) and tip member (524) may thus cooperate to form an illuminating feature like illuminating features (344, 454) described above. In some other variations, an LED or other light source is integrated into guidewire (500), at or near tip member (524), with electrical wires or conductive traces extending through lumen (512) to provide electrical power to the LED. In such variations, optical fiber (520) may be omitted.

In addition to, or as an alternative to, providing distally-oriented illumination via tip member (524), optical fiber (520) may be configured to provide a Fiber-Bragg grating sensor, which may provide strain sensing, pressure sensing, temperature sensing, and/or sensing. In cases where guidewire (500) provides pressure sensing (through a Fiber-Bragg grating sensor or otherwise), guidewire (500) may enable passive patient registration with IGS navigation system (100), such as by cross-referencing pressure increases with known landmarks in a preoperative image (e.g., CT scan) stored in processor (108).

The proximal end (not shown) of core wire (530) may be fixedly secured relative to the proximal end (not shown) of outer coil (510). Core wire (530) has a distal end (532) that is fixedly secured to tip member (524), such that distal end (532) is fixedly secured relative to the distal end of outer coil (510). While distal end (532) is secured to outer coil (510) via tip member (524) in this example, distal end (532) may be secured to outer coil (510) in any other suitable fashion. Core wire (530) of the present example is formed of a non-extensible material (e.g., steel wire, steel ribbon, one or more polymeric strands, etc.), such that core wire (530) is configured to provide tensile strength to guidewire (500). Outer coil (510) and core wire (530) together provide substantial lateral flexibility to guidewire (500), allowing guidewire (500) to be readily navigated along tortuous paths; while core wire (530) prevents outer coil (510) from stretching longitudinally.

The proximal ends (not shown) of electrical wires (542) are coupled with an electrical interface that ultimately communicates with an IGS navigation system like system (100) described above. For instance, the proximal ends of electrical wires (542) may be coupled with a feature like coupling unit (116). The distal ends of electrical wires (542) are coupled with a position sensor (540), which is further secured relative to tip member (524). Position sensor (540) may be configured and operable like any other position sensor (346, 456) described herein, such that position sensor (540) may generate signals indicating the real-time position of tip member (524) in three-dimensional space. While electrical wires (542) are used to convey signals from position sensor (540) in this example, some other variations may provide conductive traces (e.g., on a flexible circuit substrate) to convey signals from position sensor (540).

Guidewire (500) may be further configured and operable in accordance with at least some of the teachings of U.S. Pat. No. 10,772,489, entitled "Guidewire Navigation for Sinuplasty," issued Sep. 15, 2020, the disclosure of which is incorporated by reference herein, in its entirety.

IV. Example of a Dilation Instrument with Two Sliders, a Malleable Guide Member, and a Guidewire with a Ball Tip FIGS. 7A-7D show another example of a dilation instrument (600) that may be used to dilate the ostium or other drainage passageway of a paranasal sinus, to dilate a Eustachian tube, or to dilate some other anatomical passageway (e.g., within the ear, nose, or throat, etc.). By way of example only, dilation instrument (600) may be configured and operable in accordance with at least some of the teachings of any of the patent references cited herein. Dilation instrument (600) of the present example comprises a handle assembly (610) and a shaft assembly (620). Handle assembly (610) includes a body (612) that may be grasped and operated by a single hand of an operator. A port (618) extends proximally from body (612); while shaft assembly (620) extends distally from body (612). A first slider (614) is slidably positioned along body (612) and is operable to drive translation of a dilation catheter (660) relative to body (612) as will be described in greater detail below. A second slider (616) is also slidably positioned along body (612) and is operable to drive translation of a guidewire (650) relative to body (612) as will be described in greater detail below.

Shaft assembly (620) of this example includes a rigid outer guide tube (630), an inner malleable guide member (640), guidewire (650), and dilation catheter (660). Outer guide tube (630) is fixedly secured relative to handle assembly (610) and terminates in a distal end (632). Outer guide tube (630) is fully rigid in this example, such that outer guide tube (630) is not configured to bend. In some other variations, outer guide tube (630) is configured to bend. In still other variations, outer guide tube (630) is omitted. It should therefore be understood that that it is not necessary to include outer guide tube (630) in all versions of instrument (600).

Guide member (640) is positioned within outer guide tube (630) and extends distally relative to outer guide tube (630), such that a distal end (642) of guide member (640) is positioned distally relative to distal end (632) of outer guide tube (630). The proximal end of guide member (640) fixedly secured relative to handle assembly (610), such that guide member (640) does not translate relative to handle assembly (610) in this example. In some versions, a proximal portion of guide member (640) is rigid. At least a distal region of guide member (640) (e.g., the region of guide member (640) that is distally exposed relative to distal end (632) of outer guide tube (632)) is malleable such that guide member (640) may be manually bent to achieve a desired bend angle; and maintain that bend angle as guide member (640) is inserted through a nasal cavity (or other access site) to reach a targeted anatomical opening or other anatomical passageway. Guide member (640) thus has sufficient flexibility to bend to form a desired bend angle; while having sufficient rigidity to maintain the desired bend angle during a dilation procedure. Use of instrument (600) in a dilation procedure will thus not cause guide member (640) to undesirably unbend or re-bend. By way of example only, guide member (640) may comprise a metallic hypotube. While guide member (640) is shown as being straight in FIGS. 7A-7D, guide member (640) may be bent to achieve any desired bend angle.

Dilation catheter (660) is slidably disposed within a radial gap formed between the inner diameter of outer guide tube (630) and the outer diameter of guide member (640), such that dilation catheter (660) is positioned internally relative to guide tube (630) and externally relative to guide member (640). The proximal portion of dilation catheter (660) is fixedly secured to slider (614), such that slider (614) is operable to drive longitudinal translation of dilation catheter (660) relative to body (612). Dilation catheter (660) includes an inflatable balloon (664) near a distal end (662) of dilation catheter (660). Balloon (664) is fluidically coupled with port (618), such that an inflation fluid (e.g., saline, etc.) may be communicated to or from port (618) to selectively inflate or deflate balloon (664), respectively. In some versions, balloon (664) comprises a non-extensible material; while in other versions, balloon (664) comprises an extensible material. Balloon (664) is configured such that, in a deflated state (FIG. 7C), balloon (664) may be slidably positioned in a paranasal sinus ostium, another drainage passageway of a paranasal sinus, a Eustachian tube, or some other anatomical passageway. Balloon (664) is further configured such that, in an inflated state (FIG. 7D), balloon (664) will dilate the opening or other passageway in which balloon (664) is disposed.

Guidewire (650) is slidably disposed within dilation catheter (660), such that guidewire (650) is positioned internally relative to dilation catheter (660). The proximal portion of guidewire (650) is fixedly secured to slider (616), such that slider (616) is operable to drive longitudinal translation of guidewire (650) relative to body (612). Guidewire (650) includes a ball tip (652) at the distal end of guidewire (650). Ball tip (652) is positioned distally relative to distal ends (632, 642, 662) of other components of shaft assembly (620), such that ball tip (652) presents the distal-most feature of shaft assembly (620) in this example. In some versions, ball tip (652) is substantially spherical. In some other versions, ball tip (652) has a shape similar to that of a blueberry. Alternatively, ball tip (652) may have any other suitable configuration. In the present example, ball tip (652) is small enough to allow ball tip (652) to traverse a paranasal sinus ostium, another drainage passageway of a paranasal sinus, or a Eustachian tube; yet is large enough to prevent ball tip (652) from traversing an isthmus between a Eustachian tube and a middle ear region of a patient. In some other variations, ball tip (652) is omitted. In some such variations, the distal tip of guidewire (650) is still atraumatic but is not enlarged.

While not shown in FIGS. 7A-7D, ball tip (652) may include an illuminating feature and/or a position sensor. An illuminating feature of ball tip (652) may be configured and operable like any of the illuminating features (344, 454, 522, 524) described herein. Similarly, a position sensor of ball tip (652) may be configured and operable like any of the position sensors (346, 456, 540) described herein.

Figure 7A:
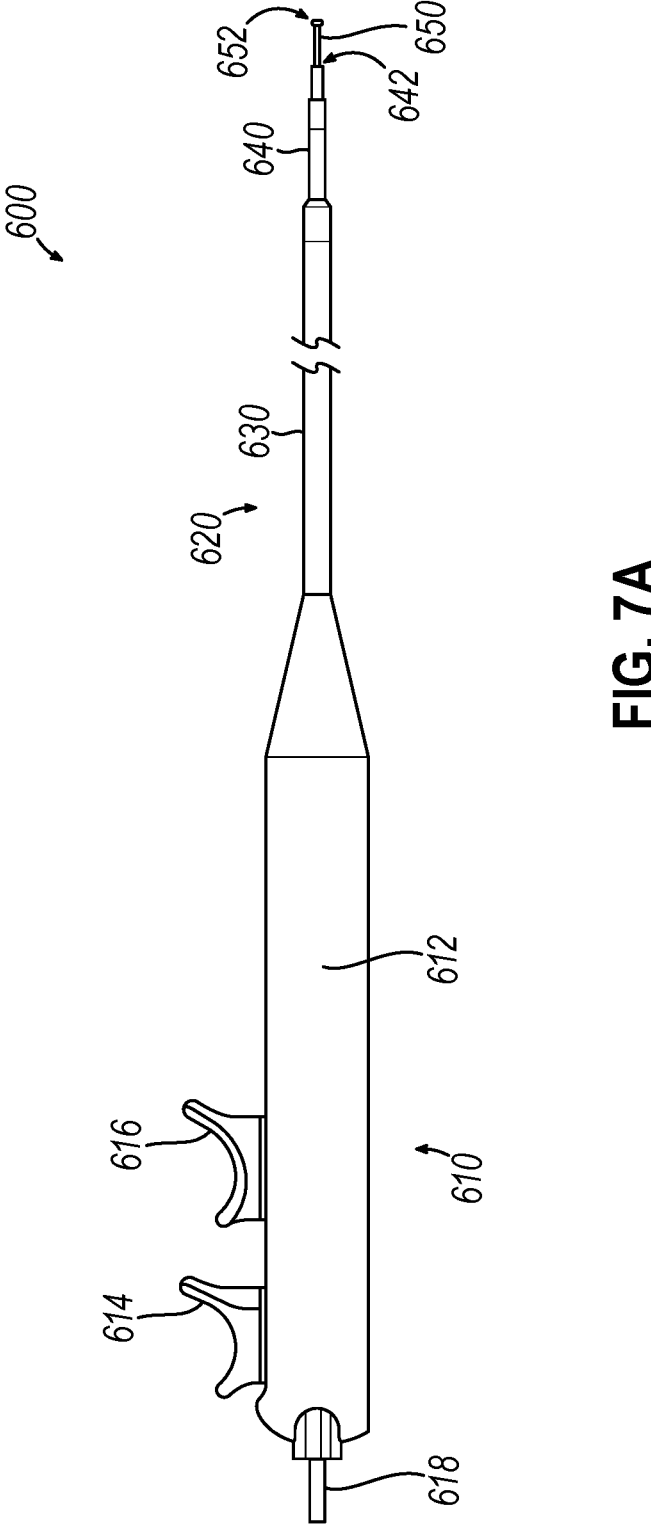
FIG. 7A depicts a side elevational view of another example of a dilation instrument, with a guidewire in a proximal position, and with a dilation catheter in a proximal position.

In an example of a use of instrument (600), the operator may form a desired bend in guide member (640) before inserting guidewire (650) and guide member (640) into the patient. This bending step may be performed while sliders (614, 616), guidewire (650), and dilation catheter (660) are proximally positioned as shown in FIG. 7A. As shown in FIG. 7A, ball tip (652) is positioned at distal end (642) of guide member (640) when guidewire (650) is in the proximal position in this example. As noted above, FIG. 7A shows guide member (640) in a straight configuration, though it should be understood that guide member (640) may instead define any suitable bend angle (e.g., based on the location and access path of the targeted anatomical opening or other anatomical passageway).

Figure 7B:
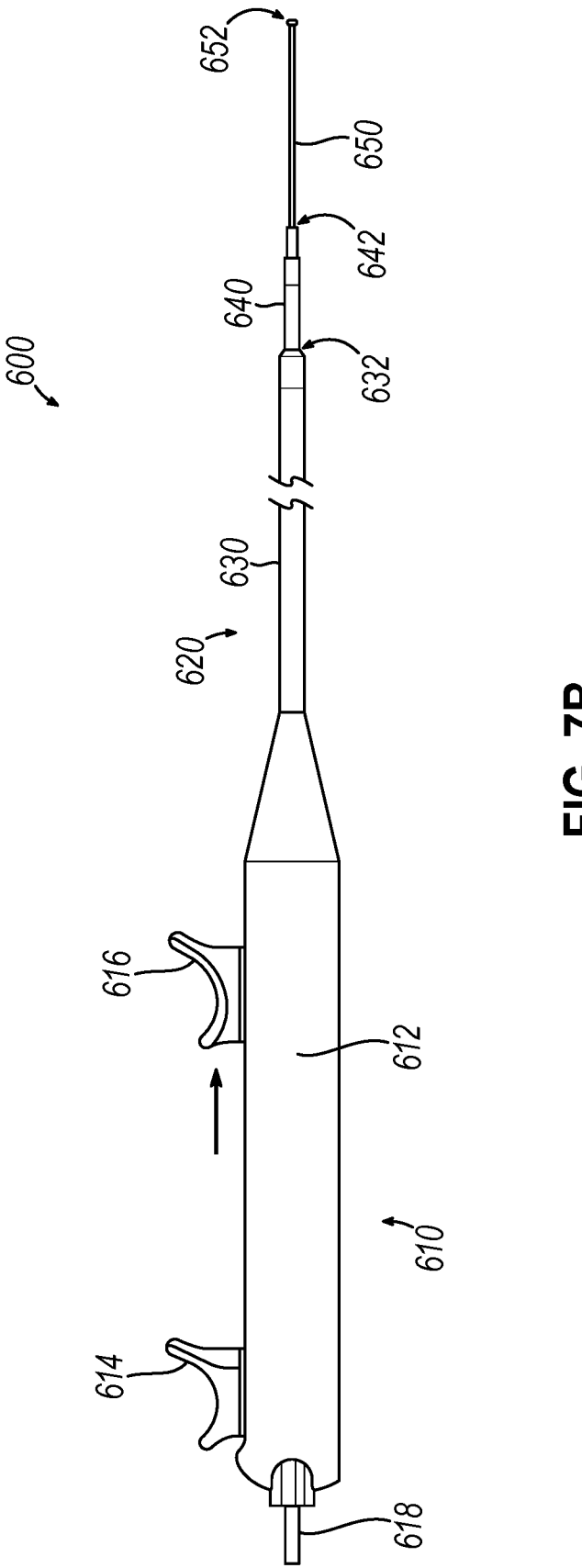
FIG. 7B depicts a side elevational view of the dilation instrument of FIG. 7A, with the guidewire in a distal position, and with the dilation catheter in the proximal position.

After the desired bend angle has been formed in guide member (640) the operator may insert shaft assembly (620) into the nasal cavity or other access passageway; and then advance slider (616) distally relative to body (612) to thereby drive guidewire (650) distally relative to body (612) as shown in FIG. 7B. Guidewire (650) may follow the bend formed by guide member (640) as guidewire (650) is advanced distally through guide member (640). The distal advancement of guidewire (650) may ultimately drive guidewire (650) into the targeted anatomical opening or other anatomical passageway. This insertion may be performed while dilation catheter (660) remains in the proximal position. In some cases, the operator only drives guidewire (650) into the targeted anatomical opening or other anatomical passageway, without also advancing guide member (640) through the targeted anatomical opening or other anatomical passageway. In some other cases, the operator drives a distal portion of guide member (640) through the targeted anatomical opening or other anatomical passageway after guidewire (650) has traversed the targeted anatomical opening or other anatomical passageway. In either scenario, the operator may rely on transillumination from ball tip (652), and/or feedback from IGS navigation system (100) based on signals from a position sensor in ball tip (652), to confirm that guidewire (650) has been appropriately positioned in relation to the targeted anatomical opening or other anatomical passageway.

Figure 7C:
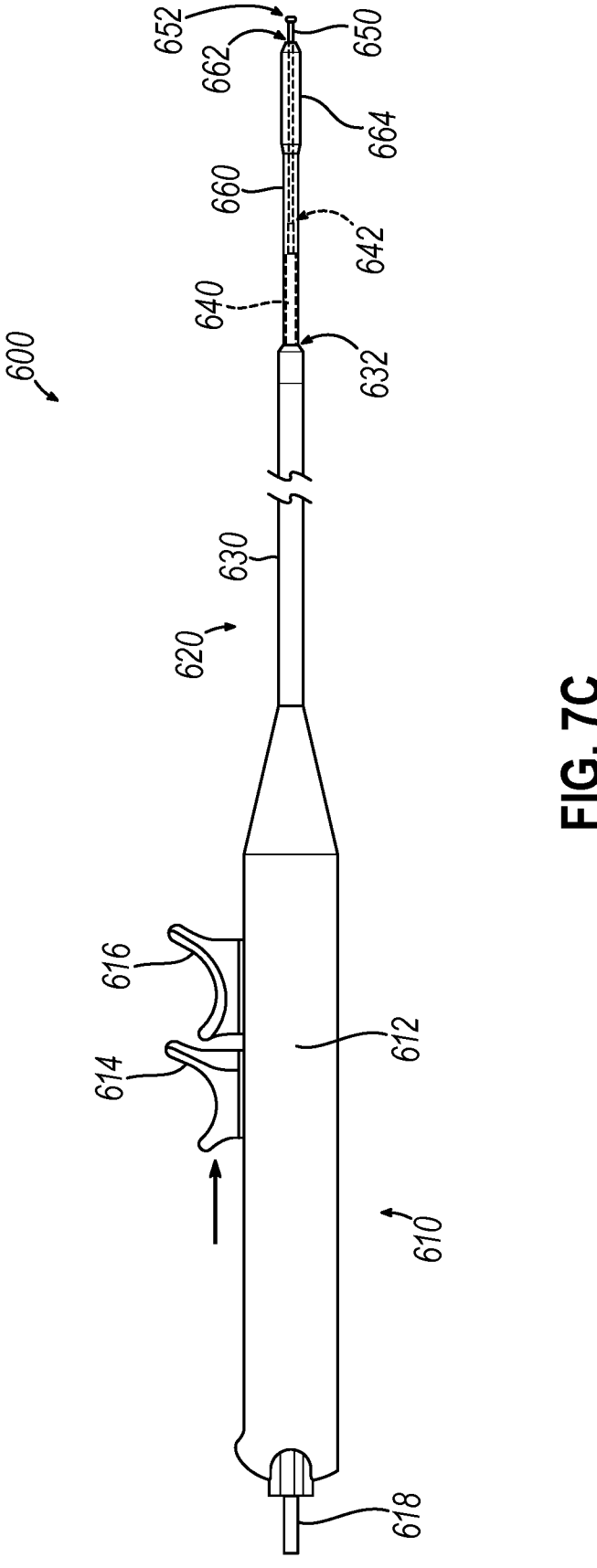
FIG. 7C depicts a side elevational view of the dilation instrument of FIG. 7A, with the guidewire in the distal position, with the dilation catheter in a distal position, and with a balloon of the dilation catheter in a deflated state.

After guidewire (650) has suitably traversed the targeted anatomical opening or other anatomical passageway, the operator may hold body (612) stationary while advancing slider (614) distally, thereby advancing dilation catheter (660) along guide member (640), and further along guidewire (650), until slider (614) and dilation catheter (660) reach a distal position as shown in FIG. 7C. It should be understood that, after distal end (662) and balloon (664) translate past distal end (642) of guide member (640), distal end (662) and balloon (664) translate along guidewire (650). It should also be understood that, in some versions, if distal end (662) of dilation catheter (660) encounters ball tip (652) during distal advancement of dilation catheter (660), ball tip (652) will prevent distal end (662) of dilation catheter (660) from advancing distally past ball tip (652). In other words, ball tip (652) may serve two purposes in some scenarios, including preventing guidewire (650) from traversing an isthmus between a Eustachian tube and a middle ear region of a patient and preventing dilation catheter (660) from advancing past guidewire (650) (thereby preventing dilation catheter (660) from traversing the isthmus).

Figure 7D:
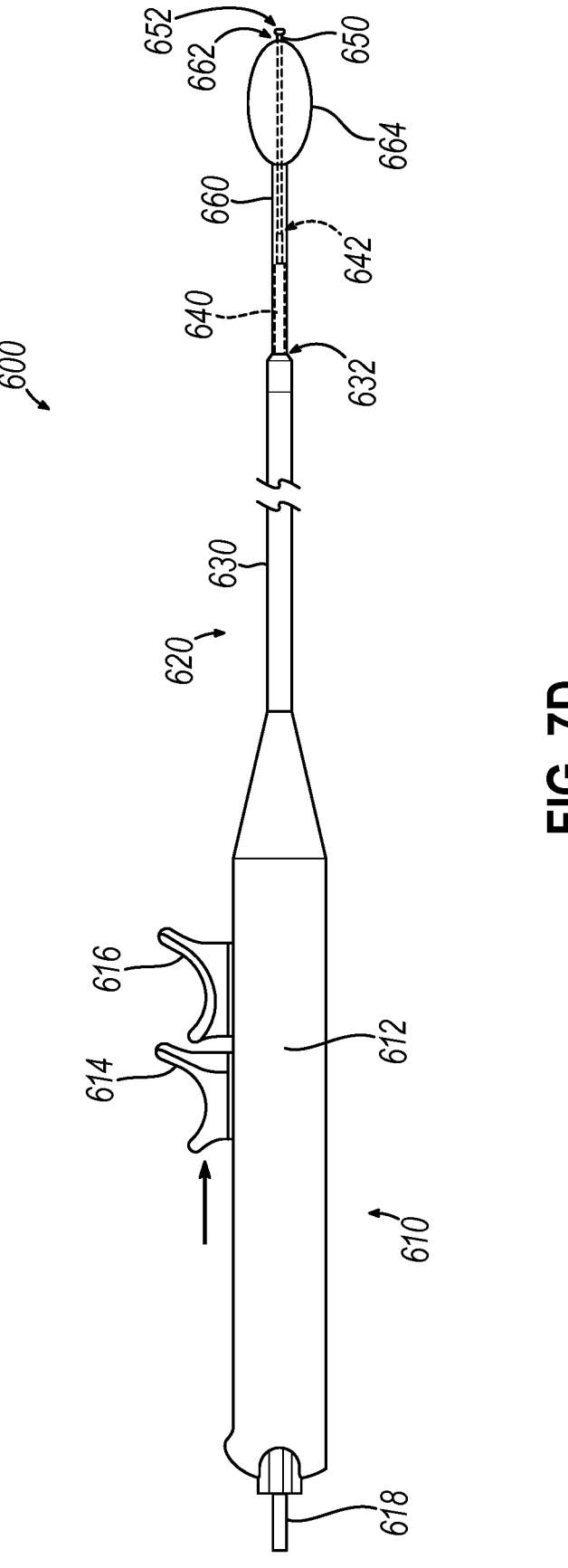
FIG. 7D depicts a side elevational view of the dilation instrument of FIG. 7A, with the guidewire in the distal position, with the dilation catheter in the distal position, and with a balloon of the dilation catheter in an inflated state.

As dilation catheter (660) advances to the distal position shown in FIG. 7C, dilation catheter (660) may advance into the targeted anatomical opening or other anatomical passageway, such that balloon (664) may be positioned the targeted anatomical opening or other anatomical passageway. It should be understood that balloon (664) may remain in the deflated state during this positioning of balloon (664) in the targeted anatomical opening or other anatomical passageway. After balloon (664) has been suitably positioned in the targeted anatomical opening or other anatomical passageway, balloon (664) may be inflated as shown in FIG. 7D. As noted above, such inflation may be provided by communicating fluid (e.g., saline, etc.) via port (618). The inflated balloon (664) may dilate the targeted anatomical opening or other anatomical passageway. The operator may maintain the inflated state of balloon (664) for any desired duration while balloon (664) is disposed in the targeted anatomical opening or other anatomical passageway. Balloon (664) may then be deflated. In some scenarios, the operator may repeatedly inflate and deflate balloon (664) while balloon (664) is disposed in the targeted anatomical opening or other anatomical passageway. After the targeted anatomical opening or other anatomical passageway has been sufficiently dilated by balloon (664), the operator may remove shaft assembly (620) from the patient while balloon (664) is in a deflated state. In some scenarios, the operator may bend guide member (640) again to achieve a different bend angle, then repeat the steps described above to dilate another anatomical opening or other anatomical passageway in the patient.

In addition to, or as an alternative to, the use of instrument (600) described above, instrument (600) may be used as a seeker device and/or to atraumatically move tissue within the ear, nose, or throat of the patient. For instance, guide member (640) may be bent to a desired bend angle, and ball tip (652) (e.g., while remaining positioned at distal end (642) of guide member (640)) may be utilized to probe tissue within an anatomical cavity, to move tissue within an anatomical cavity, or to otherwise engage tissue in an anatomical cavity. This may be done before, during, and/or after a dilation procedure as described above. This may also be done even in procedures where no dilation is performed. Thus, instrument (600) may provide clinically meaningful uses even in scenarios where dilation catheter (660) is not utilized.

V. Example of a Dilation Instrument with One Slider, a Malleable Guide Member, and a Guidewire with a Ball Tip FIGS. 8A-8D show another example of a dilation instrument (700) that may be used to dilate the ostium or other drainage passageway of a paranasal sinus, to dilate a Eustachian tube, or to dilate some other anatomical passageway (e.g., within the ear, nose, or throat, etc.). By way of example only, dilation instrument (700) may be configured and operable in accordance with at least some of the teachings of any of the patent references cited herein. Dilation instrument (700) of the present example comprises a handle assembly (710) and a shaft assembly (720). Handle assembly (710) includes a body (712) that may be grasped and operated by a single hand of an operator. A port (718) extends proximally from body (712); while shaft assembly (720) extends distally from body (712). A slider (714) is slidably positioned along body (712) and is operable to drive translation of a dilation catheter (760) relative to body (712) as will be described in greater detail below.

Shaft assembly (720) of this example includes a rigid outer guide tube (730), an inner malleable guide member (740), guidewire (750), and dilation catheter (760). Outer guide tube (730) is fixedly secured relative to handle assembly (710) and terminates in a distal end (732). Outer guide tube (730) is fully rigid in this example, such that outer guide tube (730) is not configured to bend. In some other variations, outer guide tube (730) is configured to bend. In still other variations, outer guide tube (730) is omitted. It should therefore be understood that that it is not necessary to include outer guide tube (730) in all versions of instrument (700).

Guide member (740) is positioned within outer guide tube (730) and extends distally relative to outer guide tube (730), such that a distal end (742) of guide member (740) is positioned distally relative to distal end (732) of outer guide tube (730). The proximal end of guide member (740) fixedly secured relative to handle assembly (710), such that guide member (740) does not translate relative to handle assembly (710) in this example. In some versions, a proximal portion of guide member (740) is rigid. At least a distal region of guide member (740) (e.g., the region of guide member (740) that is distally exposed relative to distal end (732) of outer guide tube (732)) is malleable such that guide member (740) may be manually bent to achieve a desired bend angle; and maintain that bend angle as guide member (740) is inserted through a nasal cavity (or other access site) to reach a targeted anatomical opening or other anatomical passage-way. Guide member (740) thus has sufficient flexibility to bend to form a desired bend angle; while having sufficient rigidity to maintain the desired bend angle during a dilation procedure. Use of instrument (700) in a dilation procedure will thus not cause guide member (740) to undesirably unbend or re-bend. By way of example only, guide member (740) may comprise a metallic hypotube. While guide member (740) is shown as being straight in FIGS. 8A-8D, guide member (740) may be bent to achieve any desired bend angle.

Dilation catheter (760) is slidably disposed within a radial gap formed between the inner diameter of outer guide tube (730) and the outer diameter of guide member (740), such that dilation catheter (760) is positioned internally relative to guide tube (730) and externally relative to guide member (740). The proximal portion of dilation catheter (760) is fixedly secured to slider (714), such that slider (714) is operable to drive longitudinal translation of dilation catheter (760) relative to body (712). Dilation catheter (760) includes an inflatable balloon (764) near a distal end (762) of dilation catheter (760). Balloon (764) is fluidically coupled with port (718), such that an inflation fluid (e.g., saline, etc.) may be communicated to or from port (718) to selectively inflate or deflate balloon (764), respectively. In some versions, bal-loon (764) comprises a non-extensible material; while in other versions, balloon (764) comprises an extensible mate-rial. Balloon (764) is configured such that, in a deflated state (FIG. 8B), balloon (764) may be slidably positioned in a paranasal sinus ostium, another drainage passageway of a paranasal sinus, a Eustachian tube, or some other anatomical passageway. Balloon (764) is further configured such that, in an inflated state (FIG. 8C), balloon (764) will dilate the opening or other passageway in which balloon (764) is disposed.

Guidewire (750) is slidably disposed within dilation cath-eter (760), such that guidewire (750) is positioned internally relative to dilation catheter (760). Unlike guidewire (650) of instrument (600), guidewire (750) of instrument (700) is not secured to a slider. Instead, guidewire (750) is driven longitudinally by translation of dilation catheter (760) as described below. Guidewire (750) includes a ball tip (752) at the distal end of guidewire (750). Ball tip (752) is positioned distally relative to distal ends (732, 742, 762) of other components of shaft assembly (720), such that ball tip (752) presents the distal-most feature of shaft assembly (720) in this example. In some versions, ball tip (752) is substantially spherical. In some other versions, ball tip (752) has a shape similar to that of a blueberry. Alternatively, ball tip (752) may have any other suitable configuration. In the present example, ball tip (752) is small enough to allow ball tip (752) to traverse a paranasal sinus ostium, another drainage passageway of a paranasal sinus, or a Eustachian tube; yet is large enough to prevent ball tip (752) from traversing an isthmus between a Eustachian tube and a middle ear region of a patient. In some other variations, ball tip (752) is omitted. In some such variations, the distal tip of guidewire (750) is still atraumatic but is not enlarged.

While not shown in FIGS. 8A-8D, ball tip (752) may include an illuminating feature and/or a position sensor. An illuminating feature of ball tip (752) may be configured and operable like any of the illuminating features (344, 454, 522, 524) described herein. Similarly, a position sensor of ball tip (752) may be configured and operable like any of the position sensors (346, 456, 540) described herein.

Figure 8A:
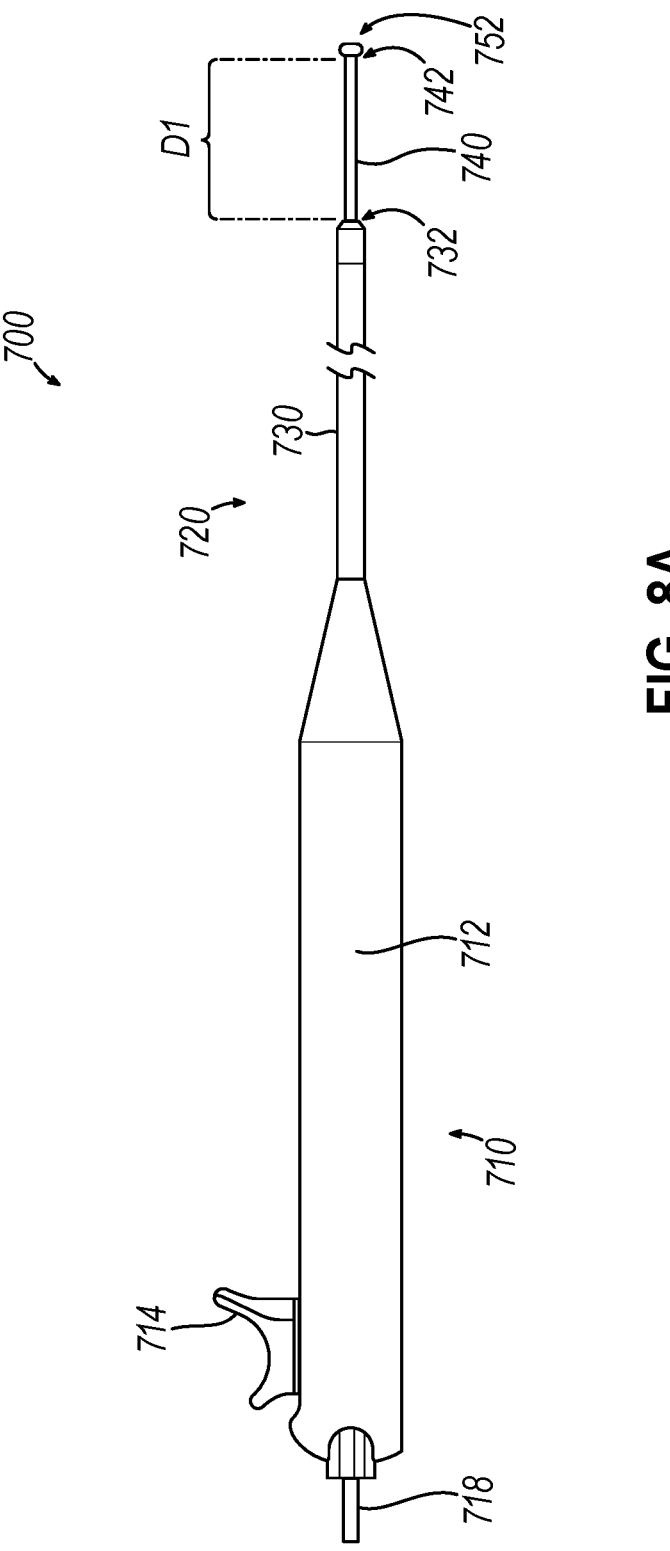
FIG. 8A depicts a side elevational view of depicts a side elevational view of another example of a dilation instrument, with a dilation catheter in a proximal position.

In an example of a use of instrument (700), the operator may form a desired bend in guide member (740) before inserting ball tip (752) and guide member (740) into the patient. This bending step may be performed while slider (714), guidewire (750), and dilation catheter (760) are proximally positioned as shown in FIG. 8A. As shown in FIG. 8A, ball tip (752) is positioned at distal end (742) of guide member (740) when guidewire (750) is in the proxi-mal position in this example. In this proximal position, ball tip (752) is at a first distance (D1) from distal end (732) of outer guide tube (730). In versions of instrument that lack guide tube (730), a first distance may instead be defined between the distal end of body (712) and ball tip (752). As noted above, FIG. 8A shows guide member (740) in a straight configuration, though it should be understood that guide member (740) may instead define any suitable bend angle (e.g., based on the location and access path of the targeted anatomical opening or other anatomical passage-way).

After the desired bend angle has been formed in guide member (740) the operator may insert shaft assembly (720) into the nasal cavity or other access passageway. In some cases, the operator further advances ball tip (752) and a distal portion of guide member (740) into the targeted anatomical opening or other anatomical passageway, such that ball tip (752) and a distal portion of guide member (740) traverse the targeted anatomical opening or other anatomical passageway. In some other cases, the operator advances ball tip (752) to a position adjacent to the targeted anatomical opening or other anatomical passageway; but stops just short of advancing ball tip (752) into the targeted anatomical opening or other anatomical passageway, such that ball tip (752) and a distal portion of guide member (740) do not traverse the targeted anatomical opening or other anatomical passageway. In either scenario, the insertion may be per-formed while dilation catheter (760) remains in the proximal position. The operator may rely on transillumination from ball tip (752), and/or feedback from IGS navigation system (100) based on signals from a position sensor in ball tip (752), to confirm that guide member (740) has been appro-priately positioned in relation to the targeted anatomical opening or other anatomical passageway.

Figure 8B:
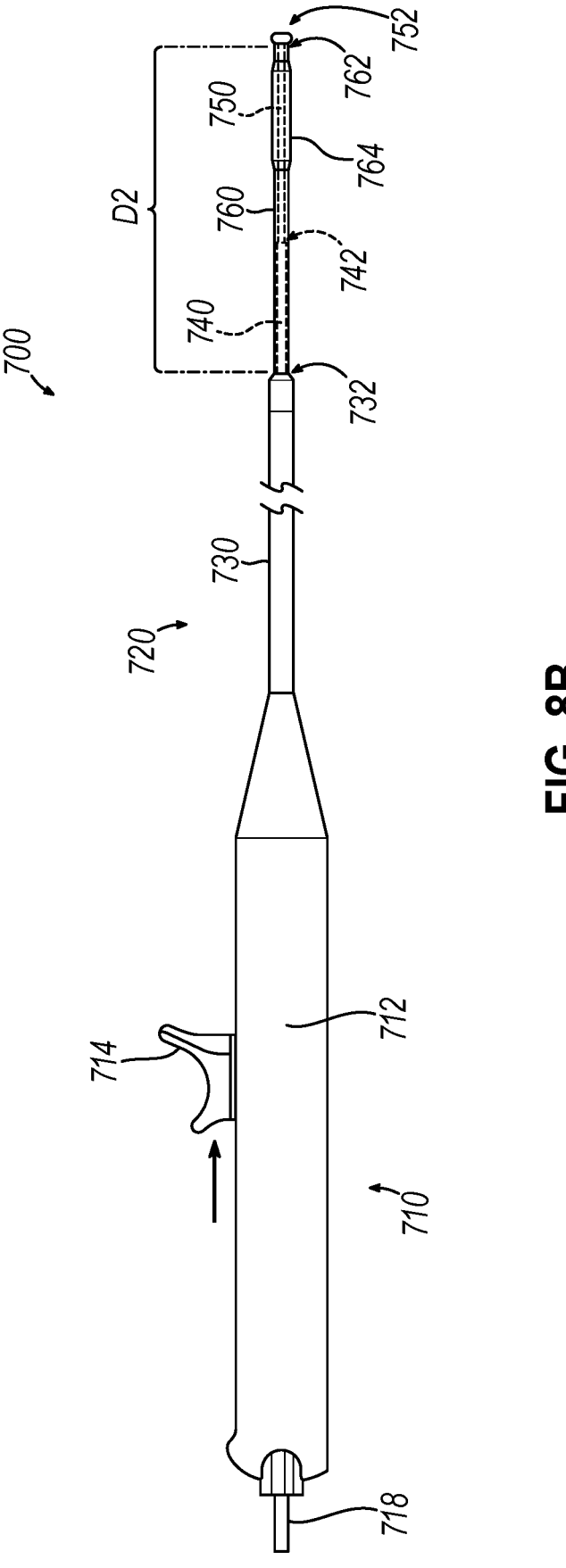
FIG. 8B depicts a side elevational view of the dilation instrument of FIG. 8A, with the dilation catheter in a distal position, and with a balloon of the dilation catheter in a deflated state.

After ball tip (752) has been appropriately positioned in relation to the targeted anatomical opening or other ana-tomical passageway, the operator holds body (712) station-ary and advances slider (714) distally relative to body (712) to thereby drive dilation catheter (760) distally relative to body (712), as shown in FIG. 8B. Dilation catheter (760) may follow the bend formed by guide member (740) as dilation catheter (760) is advanced distally along guide member (740). As dilation catheter (760) is advanced dis-tally, the distal end (762) of dilation catheter (760) engages ball tip (752). With distal end (762) of dilation catheter (760) engaging ball tip (752), dilation catheter (760) pushes ball tip (752) and the rest of guidewire (750) distally. In other words, ball tip (752) and the rest of guidewire (750) translate distally relative to body (712) with dilation catheter (760). At this stage, ball tip (752) is at a second distance (D2) from distal end (732) of outer guide tube (730). In versions of instrument that lack guide tube (730), a second distance may instead be defined between the distal end of body (712) and ball tip (752). The distal advancement of dilation catheter (760) and ball tip (752) may ultimately drive ball tip (752) through the targeted anatomical opening or other anatomical passageway; and balloon (764) into the targeted anatomical opening or other anatomical passageway. In other words, as dilation catheter (760) advances to the distal position shown in FIG. 8B, dilation catheter (760) may advance into the targeted anatomical opening or other anatomical passageway, such that balloon (764) may be positioned the targeted anatomical opening or other anatomical passageway. Balloon (764) may remain in the deflated state during this positioning of balloon (764) in the targeted anatomical opening or other anatomical passageway.

It should be understood that ball tip (752) will prevent distal end (762) of dilation catheter (760) from advancing distally past ball tip (752). Moreover, ball tip (752) may prevent dilation catheter (760) from traversing the isthmus between a Eustachian tube and a middle ear region of a patient. It should also be understood that the operator may rely on transillumination from ball tip (752), and/or feedback from IGS navigation system (100) based on signals from a position sensor in ball tip (752), to confirm that dilation catheter (760) has been appropriately positioned in relation to the targeted anatomical opening or other anatomical passageway.

In some versions, handle assembly (710) includes one or more features configured to provide tactile, audible, and/or visual feedback to the operator indicating when distal end (762) of dilation catheter (760) has engaged ball tip (752), such that further advancement of dilation catheter (760) will cause distal advancement of ball tip (752) and dilation catheter (750). For instance, the proximal end of guidewire (750) may include a detent feature that engages a complementary detent feature within handle assembly (710). Such detent features may prevent inadvertent distal advancement of guidewire (750) relative to body (712); yet may permit distal advancement of guidewire (750) relative to body (712) when dilation catheter (760) is advanced distally after distal end (762) of dilation catheter (760) has engaged ball tip (752). Moreover, such detent features may provide tactile feedback (e.g., a slight resistance or clicking feel, etc.) and/or audible feedback (e.g., a clicking sound, etc.) when dilation catheter (760) is advanced distally after distal end (762) of dilation catheter (760) has engaged ball tip (752). As another example, a hall effect sensor or other kind of proximity sensor, reed switch, optical sensor, or other feature may be configured to generate an electrical signal indicating when distal end (762) of dilation catheter (760) has engaged ball tip (752). The signal generated by such a sensor may activate a haptic feedback device (e.g., vibration generator, etc.), an audible feedback device (e.g., providing a tone through a speaker, etc.), and/or a visual feedback device (e.g., an LED or a display, etc.). Alternatively, any other suitable features may be used to provide tactile, audible, and/or visual feedback to the operator indicating when distal end (762) of dilation catheter (760) has engaged ball tip (752).

Figure 8C:
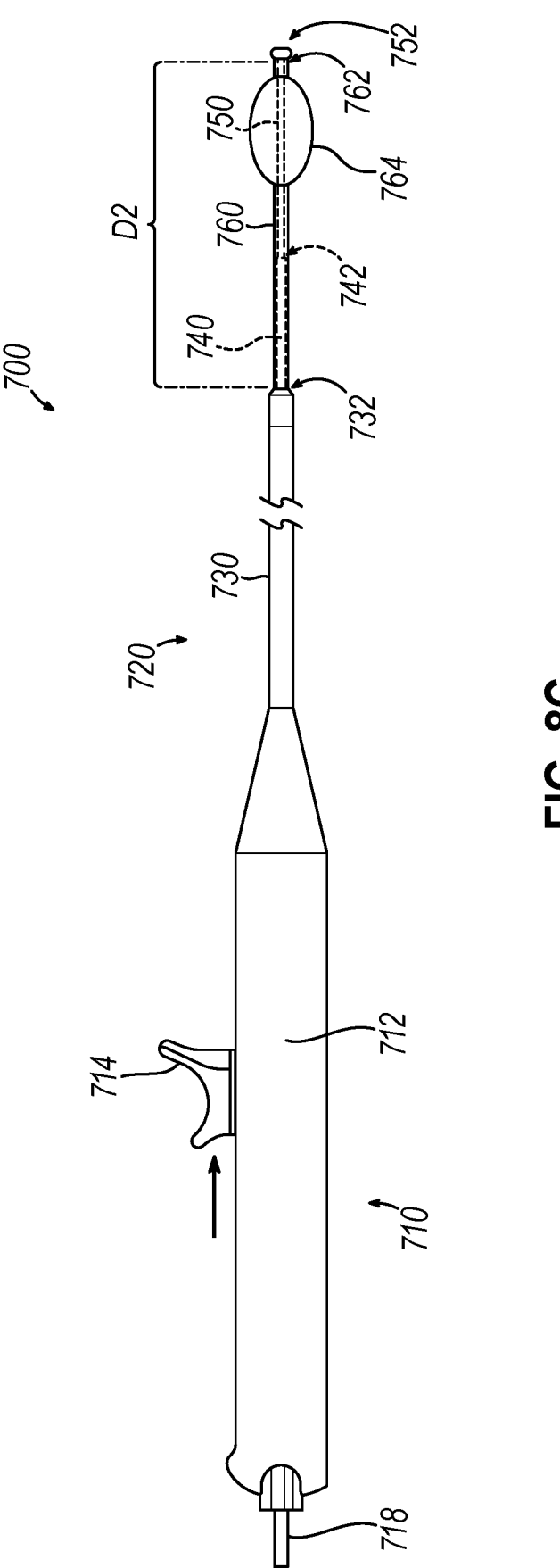
FIG. 8C depicts a side elevational view of the dilation instrument of FIG. 8A, with the dilation catheter in the distal position, and with the balloon of the dilation catheter in an inflated state.

After balloon (764) has been suitably positioned in the targeted anatomical opening or other anatomical passageway, balloon (764) may be inflated as shown in FIG. 8C. As noted above, such inflation may be provided by communicating fluid (e.g., saline, etc.) via port (718). The inflated balloon (764) may dilate the targeted anatomical opening or other anatomical passageway. The operator may maintain the inflated state of balloon (764) for any desired duration while balloon (764) is disposed in the targeted anatomical opening or other anatomical passageway. Balloon (764) may then be deflated. In some scenarios, the operator may repeatedly inflate and deflate balloon (764) while balloon (764) is disposed in the targeted anatomical opening or other anatomical passageway.

Figure 8D:
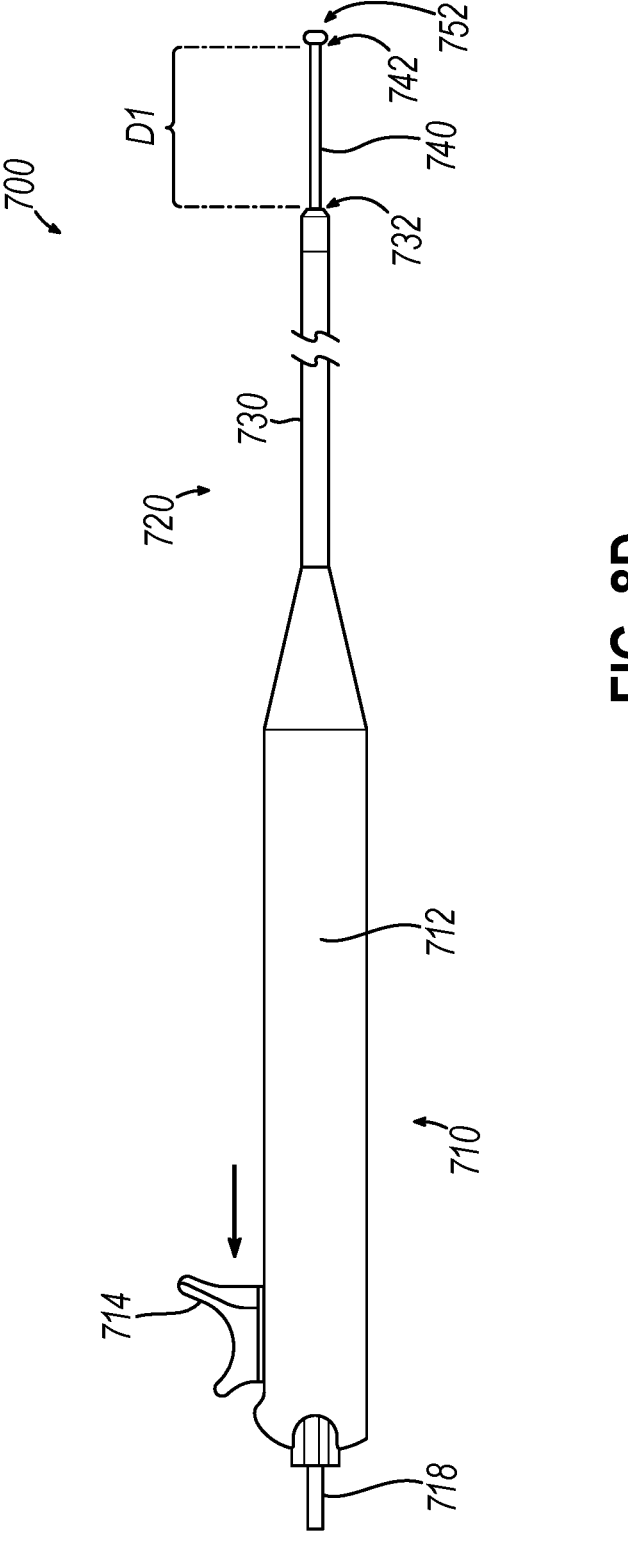
FIG. 8D depicts a side elevational view of the dilation instrument of FIG. 8A, with the dilation catheter returned to the proximal position.

After the targeted anatomical opening or other anatomical passageway has been sufficiently dilated by balloon (764), the operator may deflate balloon (764) and actuate slider (714) proximally, thereby driving dilation catheter (760)

proximally, as shown in FIG. 8D. As also shown in FIG. 8D, this proximal retraction of dilation catheter (760) may also retract guidewire (750) proximally. The concomitant retraction of dilation catheter (760) and guidewire (750) may be provided in various ways. In some versions, distal end (762) of dilation catheter (760) has a feature that selectively couples with a complementary feature of ball tip (752) or elsewhere at the distal end of guidewire (762). Such selective coupling features may be mechanical (e.g., detent features), magnetic, or be otherwise configured. Alternatively, some other portion of dilation catheter (760) (e.g., proximal to balloon (764)) may selectively couple with a complementary feature of guidewire (750).

Regardless of where the complementary coupling features of dilation catheter (760) and guidewire (750) are positioned, such complementary coupling features may engage each other after distal end (762) of dilation catheter engages ball tip (752); and may remain engaged during a certain range of proximal travel of dilation catheter (760) and guidewire (750). In particular, the complementary coupling features may remain engaged during an initial range of proximal travel of dilation catheter (760) and guidewire (750), such that dilation catheter (760) and guidewire (750) translate proximally concomitantly during this initial range of proximal travel, until ball tip (752) engages distal end (742) of guide member (740). At this point, distal end (742) of guide member (740) may arrest further proximal movement of ball tip (752) and the rest of guidewire (750), such that ball tip (752) may remain positioned at the first distance (D1) from distal end (732) of outer guide tube (730) while dilation catheter (760) continues to translate proximally relative to body (712). Thus, engagement between ball tip (752) and distal end (742) of guide member (740) during concomitant proximal retraction of dilation catheter (760) and guidewire (750) may cause the complementary coupling features of dilation catheter (760) and guidewire (750) to disengage each other.

In some variations, dilation catheter (760) and guidewire (750) are selectively coupled in accordance with at least some of the teachings of U.S. Pat. No. 11,419,623, entitled "Sinuplasty Instrument with Moveable Navigation Sensor," issued Aug. 23, 2022, the disclosure of which is incorporated by reference herein, in its entirety.

After reaching the stage shown in FIG. 8D, the operator may remove shaft assembly (720). In some scenarios, the operator may bend guide member (740) again to achieve a different bend angle, then repeat the steps described above to dilate another anatomical opening or other anatomical passageway in the patient.

In addition to, or as an alternative to, the use of instrument (700) described above, instrument (700) may be used as a seeker device and/or to atraumatically move tissue within the ear, nose, or throat of the patient. For instance, guide member (740) may be bent to a desired bend angle, and ball tip (752) (e.g., while remaining positioned at distal end (742) of guide member (740)) may be utilized to probe tissue within an anatomical cavity, to move tissue within an anatomical cavity, or to otherwise engage tissue in an anatomical cavity. This may be done before, during, and/or after a dilation procedure as described above. This may also be done even in procedures where no dilation is performed. Thus, instrument (700) may provide clinically meaningful uses even in scenarios where dilation catheter (760) is not utilized.

VI. Example of a Dilation Instrument with No Slider

Figure 9:
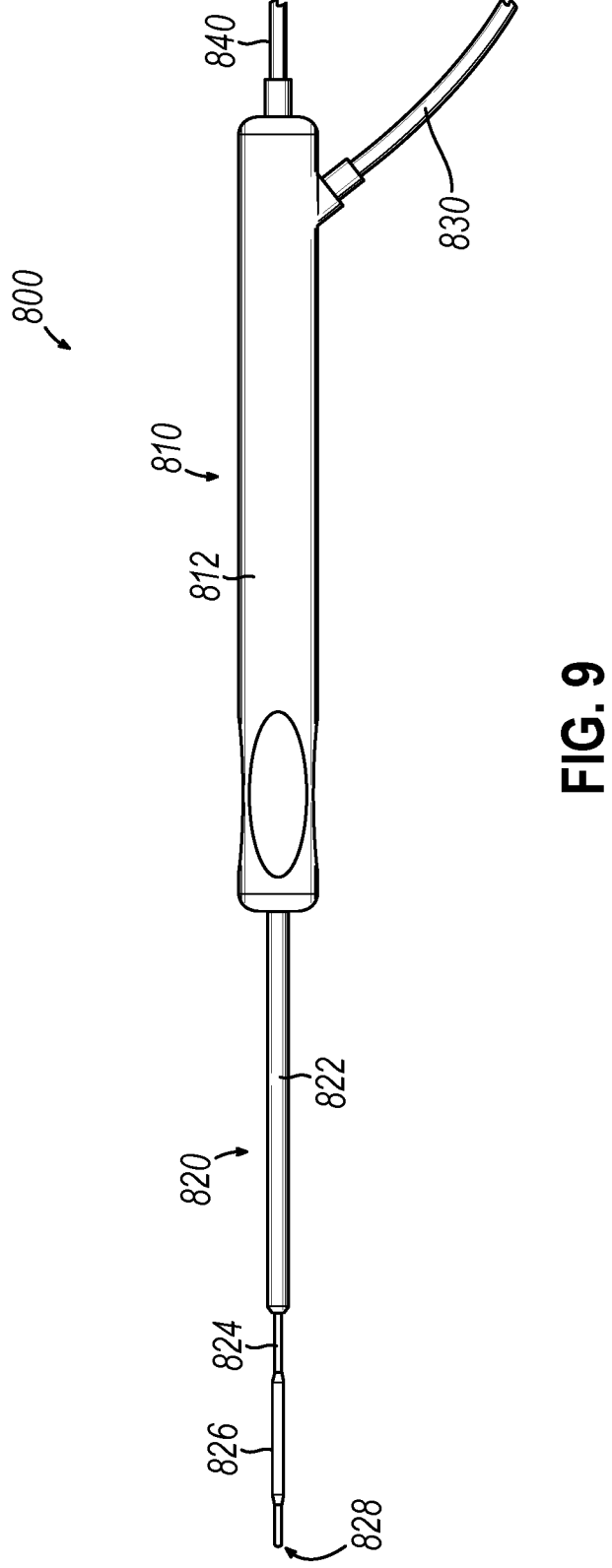
FIG. 9 depicts a side elevational view of another example of a dilation instrument.
Figure 10:
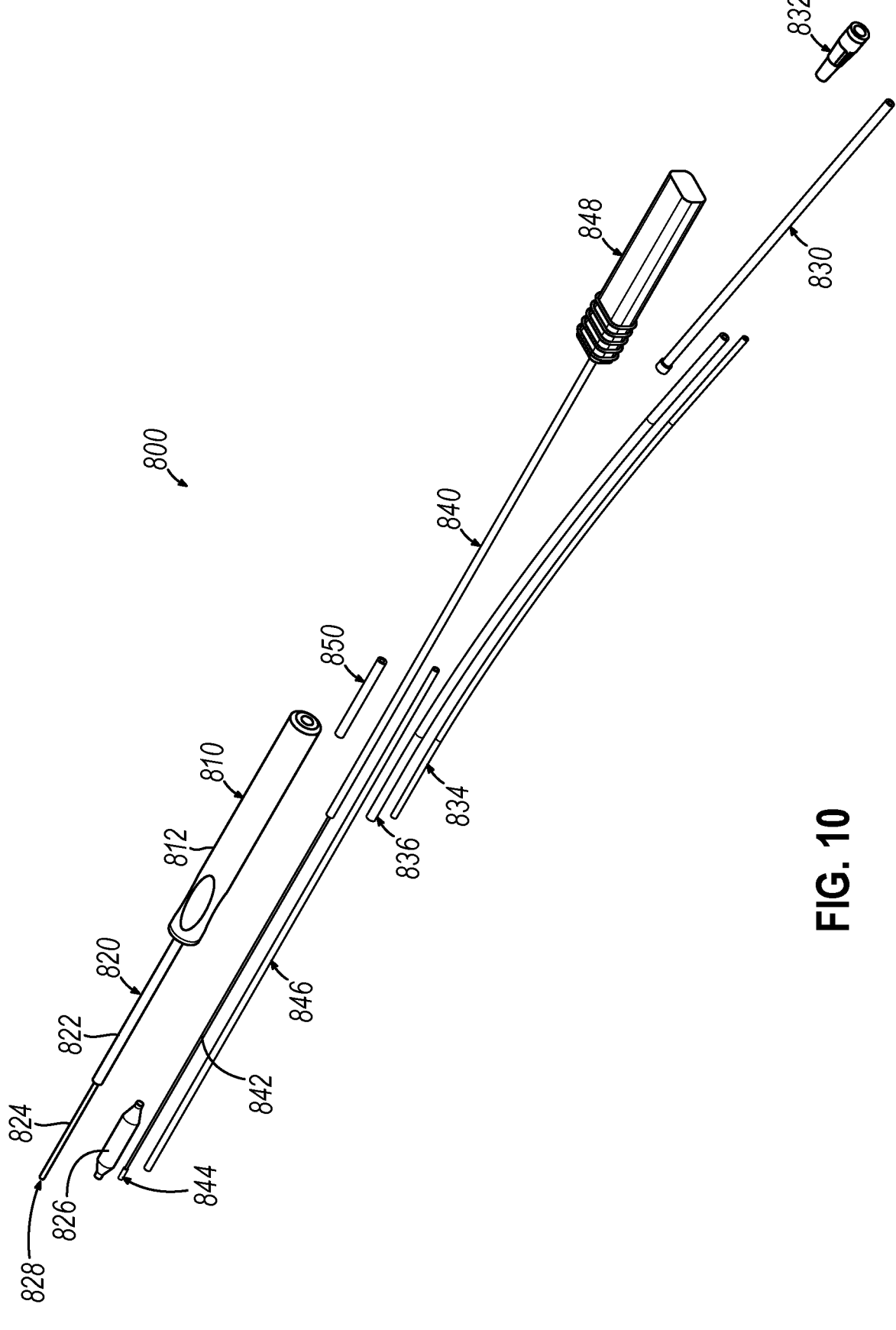
FIG. 10 depicts an exploded perspective view of the dilation instrument of FIG. 9.

FIGS. 9-10 show another example of a dilation instrument (800) that may be used to dilate the ostium or other drainage passageway of a paranasal sinus, to dilate a Eustachian tube, or to dilate some other anatomical passageway (e.g., within the ear, nose, or throat, etc.). By way of example only, dilation instrument (800) may be configured and operable in accordance with at least some of the teachings of any of the patent references cited herein. Dilation instrument (800) of the present example comprises a handle assembly (810) and a shaft assembly (820). Handle assembly (810) includes a body (812) that may be grasped and operated by a single hand of an operator. A cable (840) and an inflation tube (830) extend proximally from body (812); while shaft assembly (820) extends distally from body (812).

Shaft assembly (820) includes a rigid proximal portion (822) and a malleable distal portion (824). Portions (822, 824) are fixedly secured relative to each other and relative to body (812), such that neither portion (822, 824) translates longitudinally relative to body (812) in this example. Malleable distal portion (824) is configured to be manually bent to achieve a desired bend angle; and maintain that bend angle as distal portion (824) is inserted through a nasal cavity (or other access site) to reach a targeted anatomical opening or other anatomical passageway. Malleable distal portion (824) thus has sufficient flexibility to bend to form a desired bend angle; while having sufficient rigidity to maintain the desired bend angle during a dilation procedure. Use of instrument (800) in a dilation procedure will thus not cause distal portion (824) to undesirably unbend or re-bend. By way of example only, distal portion (824) may comprise a metallic hypotube. While distal portion (824) is shown as being straight in FIGS. 9-10, distal portion (824) may be bent to achieve any desired bend angle. In the present example, a distal end (828) of malleable distal portion (824) has an atraumatic configuration. In some versions, distal end (828) is in the form of a ball tip, like any of the ball tips (242, 342, 444, 652, 752) described herein. In some other versions, distal end (828) has some other atraumatic configuration that is not a ball tip.

A balloon (826) is fixedly secured about malleable distal portion (824), near distal end (828) of malleable distal portion (824). Balloon (826) is coupled with tubes (830, 834, 836), such that inflation fluid (e.g., saline, etc.) may be communicated along at least one of tubes (830, 834, 836) to selectively inflate balloon (826). A luer fitting (832) is secured to the proximal end of tube (830), allowing tube (830) to be readily coupled with any suitable source of inflation fluid. In some versions, balloon (826) comprises a non-extensible material; while in other versions, balloon (826) comprises an extensible material. Balloon (826) is configured such that, in a deflated state, balloon (826) may be slidably positioned in a paranasal sinus ostium, another drainage passageway of a paranasal sinus, a Eustachian tube, or some other anatomical passageway. Balloon (826) is further configured such that, in an inflated state, balloon (826) will dilate the opening or other passageway in which balloon (826) is disposed.

A navigation wire (842) is fixedly positioned within shaft assembly (820). Navigation wire (842) extends distally from cable (840). A polyimide tube (846) is positioned about navigation wire (842), within rigid and malleable portions (822, 824) of shaft assembly (820). A heat shrink tube (850) is positioned about one or more of tubes (834, 836, 846), to secure these components together. A position sensor (844) is at the distal end of navigation wire (842), within malleable distal portion (824). With instrument (800) fully assembled, position sensor (844) is positioned at distal end (828) of malleable distal portion (824). Position sensor (844) is configured to cooperate with an IGS navigation system (100) to thereby provide signals indicating the position of distal end (828) in three-dimensional space. Position sensor (844) may comprise one or more coils, as described above in the context of guidewire (120) of IGS navigation system (100). A connector (848) is positioned at the proximal end of cable (840) and includes features that are in electrical communication with position sensor (844) via wire (842) and cable (840). Connector (848) is configured to couple with IGS navigation system (100). Connector (848) may thus function similar to coupling unit (116) as described above. The operator may rely on navigation system (100) to determine the real-time position of distal end (828) in three-dimensional space, as described above in the context of tracking the position of guidewire (120), to determine balloon (826) has reached the targeted anatomical opening or other anatomical passageway.

In some versions, an illuminating feature (not shown) is positioned at distal end (828) of malleable distal portion (824). Such an illuminating feature may be configured and operable like any of the other illuminating features (344, 454, 522, 524) described herein. Such an illuminating feature may be provided in addition to, or instead of, position sensor (844).

In an example of a use of instrument (800), the operator may form a desired bend in malleable distal portion (824) before inserting shaft assembly (820) into the patient. After the desired bend angle has been formed in malleable distal portion (824) the operator may insert shaft assembly (820) into the nasal cavity or other access passageway, to thereby position balloon (826) in the targeted anatomical opening or other anatomical passageway. The operator may rely on feedback from IGS navigation system (100) to determine when balloon (826) has reached the targeted anatomical opening or other anatomical passageway, based on signals from position sensor (844). It should be understood that balloon (826) may remain in the deflated state during this positioning of balloon (826) in the targeted anatomical opening or other anatomical passageway.

After balloon (826) has been suitably positioned in the targeted anatomical opening or other anatomical passageway, balloon (826) may be inflated. As noted above, such inflation may be provided by communicating fluid (e.g., saline, etc.) via luer fitting (832). The inflated balloon (826) may dilate the targeted anatomical opening or other anatomical passageway. The operator may maintain the inflated state of balloon (826) for any desired duration while balloon (826) is disposed in the targeted anatomical opening or other anatomical passageway. Balloon (826) may then be deflated. In some scenarios, the operator may repeatedly inflate and deflate balloon (826) while balloon (826) is disposed in the targeted anatomical opening or other anatomical passageway. After the targeted anatomical opening or other anatomical passageway has been sufficiently dilated by balloon (826), the operator may remove shaft assembly (820) from the patient while balloon (826) is in a deflated state. In some scenarios, the operator may bend malleable distal portion (824) again to achieve a different bend angle, then repeat the steps described above to dilate another anatomical opening or other anatomical passageway in the patient.

In addition to, or as an alternative to, the use of instrument (800) described above, instrument (800) may be used as a seeker device and/or to atraumatically move tissue within the ear, nose, or throat of the patient. For instance, 8) may be bent to a desired bend angle, and distal end (828) may be utilized to probe tissue within an anatomical cavity, to move tissue within an anatomical cavity, or to otherwise engage tissue in an anatomical cavity. This may be done before, during, and/or after a dilation procedure as described above. This may also be done even in procedures where no dilation is performed. Thus, instrument (800) may provide clinically meaningful uses even in scenarios where dilation catheter (660) is not utilized.

VII. Example of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; and (b) a shaft assembly extending distally from the body, the shaft assembly including; (i) a malleable distal portion having a distal end, (ii) an enlarged tip positioned at the distal end of the malleable distal portion, (iii) a position sensor positioned within the enlarged tip, the position sensor being configured to generate a signal indicating a position of the enlarged tip in three-dimensional space, (iv) an illuminating element positioned within the enlarged tip, the illuminating element being configured to emit light, (v) an inflatable balloon positioned proximal to the enlarged tip, the inflatable balloon being configured to dilate a passageway in an ear, nose, or throat of a patient.

Example 2

The apparatus of Example 1, the body being configured for grasping by a single hand of an operator.

Example 3

The apparatus of any of Examples 1 through 2, the malleable distal portion being fixedly secured relative to the body.

Example 4

The apparatus of any of Examples 1 through 3, the shaft assembly further comprising a rigid proximal portion, the rigid proximal portion being positioned proximally in relation to the malleable distal portion.

Example 5

The apparatus of Example 4, the rigid proximal portion being fixedly secured relative to the body.

Example 6

The apparatus of any of Examples 1 through 5, the enlarged tip having a ball shape.

Example 7

The apparatus of Example 6, the ball shape being spherical.

Example 8

The apparatus of any of Examples 1 through 7, the shaft assembly further comprising a guidewire.

Example 9

The apparatus of Example 8, the malleable distal portion defining a lumen, the guidewire being positioned in the lumen.

Example 10

The apparatus of Example 9, the enlarged tip defining an opening.

Example 11

The apparatus of Example 10, the guidewire being translatable along the lumen and through the opening.

Example 12

The apparatus of Example 11, further comprising a first slider, the first slider being translatable along the body to drive translation of the guidewire along the lumen and through the opening.

Example 13

The apparatus of Example 12, the shaft assembly further comprising a dilation catheter, the dilation catheter being slidably positioned about the malleable distal portion, the dilation catheter including the inflatable balloon; the apparatus further comprising a second slider, the second slider being translatable along the body to drive translation of the dilation catheter along the malleable distal portion.

Example 14

The apparatus of Example 13, the first slider and the second slider being translatable along the body independently relative to each other.

Example 15

The apparatus of any of Examples 8 through 14, the guidewire having a distal end, the position sensor being positioned within the distal end of the guidewire, the distal end of the guidewire being positioned at the enlarged tip.

Example 16

The apparatus of any of Examples 8 through 15, the guidewire having a distal end, the illuminating element being positioned within the distal end of the guidewire, the distal end of the guidewire being positioned at the enlarged tip.

Example 17

The apparatus of any of Examples 8 through 16, the guidewire having a distal end, the enlarged tip being fixedly secured at the distal end of the guidewire.

Example 18

The apparatus of Example 17, the shaft assembly further comprising a dilation catheter, the dilation catheter being slidably positioned about the malleable distal portion, the dilation catheter including the inflatable balloon; the apparatus further comprising a slider, the slider being translatable along the body to drive translation of the dilation catheter along the malleable distal portion.

Example 19

The apparatus of Example 18, the malleable distal portion defining a lumen, the guidewire being slidably positioned in the lumen, the dilation catheter having a distal end configured to engage the enlarged tip to thereby drive distal translation of the guidewire and the enlarged tip relative to the malleable distal portion as the dilation catheter translates distally relative to the malleable distal portion.

Example 20

The apparatus of Example 19, the dilation catheter further including a first engagement feature, one or both of the guidewire or the enlarged tip including a second engagement feature, the first and second engagement features being configured to couple with each other to thereby cause the dilation catheter to drive proximal translation of the guidewire and the enlarged tip relative to the malleable distal portion as the dilation catheter translates proximal relative to the malleable distal portion.

Example 21

The apparatus of any of Examples 1 through 20, the shaft assembly further comprising a dilation catheter, the dilation catheter being slidably positioned about the malleable distal portion, the dilation catheter including the inflatable balloon.

Example 22

The apparatus of Example 21, the dilation catheter including a rigid proximal portion and a flexible distal portion, the flexible distal portion including the inflatable balloon.

Example 23

The apparatus of any of Examples 21 through 22, further comprising a slider, the slider being translatable along the body to drive translation of the dilation catheter along the malleable distal portion.

Example 24

The apparatus of any of Examples 1 through 23, the position sensor comprising a coil.

Example 25

The apparatus of any of Examples 1 through 24, the illuminating element comprising an LED.

Example 26

The apparatus of any of Examples 1 through 25, the illuminating element comprising an optical fiber.

Example 27

The apparatus of Example 26, the illuminating element further comprising a distally facing optically transmissive element in optical communication with the optical fiber.

Example 28

An apparatus comprising: (a) a body; (b) a shaft assembly extending distally from the body, the shaft assembly including; (i) a malleable distal portion having a distal end, (ii) a guidewire slidably disposed within the malleable distal portion, the guidewire including: (A) an enlarged tip, and (B) a position sensor positioned within the enlarged tip, the position sensor being configured to generate a signal indicating a position of the enlarged tip in three-dimensional space, (v) a dilation catheter slidably positioned about the malleable distal portion, the dilation catheter having a distal end and an inflatable balloon positioned proximal to the distal end of the dilation catheter, the inflatable balloon being configured to dilate a passageway in an ear, nose, or throat of a patient; and (c) an actuator, the actuator being operable to drive translation of the dilation catheter along the malleable distal portion; the distal end of the dilation catheter being configured to engage the enlarged tip to thereby drive distal translation of the guidewire and the enlarged tip relative to the malleable distal portion as the dilation catheter translates distally relative to the malleable distal portion.

Example 29

The apparatus of Example 28, the shaft assembly further including an illuminating element positioned within the enlarged tip, the illuminating element being configured to emit light.

Example 30

The apparatus of any of Examples 28 through 29, the dilation catheter further including a first engagement feature, one or both of the guidewire or the enlarged tip including a second engagement feature, the first and second engagement features being configured to couple with each other to thereby cause the dilation catheter to drive proximal translation of the guidewire and the enlarged tip relative to the malleable distal portion as the dilation catheter translates proximal relative to the malleable distal portion.

Example 31

The apparatus of Example 30, the distal end of the malleable distal portion being configured to engage the enlarged tip and thereby arrest proximal movement of the enlarged tip and guidewire.

Example 32

The apparatus of Example 31, the dilation catheter being translatable between a proximal position and a distal position, the distal end of the dilation catheter being proximal to the distal end of the malleable distal portion when the dilation catheter is in the proximal position, the distal end of the dilation catheter being distal to the distal end of the malleable distal portion when the dilation catheter is in the distal position.

Example 33

The apparatus of Example 32, the dilation catheter and the enlarged tip being configured to cooperate to position the enlarged tip distally in relation to the distal end of the malleable distal portion when the dilation catheter is in the distal position.

Example 34

The apparatus of any of Examples 32 through 33, the distal end of the malleable distal portion being configured to cooperate to position the enlarged tip at the distal end of the malleable distal portion when the dilation catheter is in the proximal position.

Example 35

The apparatus of Example 34, the distal end of the malleable distal portion being configured to cooperate to decouple the first and second engagement features from each other as the dilation catheter travels from the distal position to the proximal position.

Example 36

The apparatus of any of Examples 28 through 35, the actuator comprising a slider.

Example 37

A method comprising: (a) inserting a distal portion of a shaft assembly into an ear, nose, or throat of a patient, the shaft assembly including a dilation catheter, a malleable shaft portion, and a guidewire, the dilation catheter being slidably positioned about the malleable shaft portion, the dilation catheter including a balloon, the guidewire being slidably disposed in the malleable shaft portion, the guidewire having an enlarged tip; (b) driving the dilation catheter distally in relation to the malleable shaft portion through a range of motion, the range of motion being from a proximal position to a distal position, a distal end of the dilation catheter engaging the enlarged tip of the guidewire as the dilation catheter translates distally from the proximal position to the distal position, the distal end of the dilation catheter driving the guidewire distally via the enlarged tip as the dilation catheter advances distally to the distal position; (c) inflating the balloon of the dilation catheter while the dilation catheter is at the distal position; and (d) driving the dilation catheter proximally in relation to the malleable shaft portion from the distal position.

Example 38

The method of Example 37, further comprising forming a bend in the malleable shaft portion before inserting the distal portion of the shaft assembly into the ear, nose, or throat of the patient.

Example 39

The method of any of Examples 37 through 38, the act of driving the dilation catheter distally including driving an actuator relative to a body of a handle assembly.

Example 40

The method of any of Examples 37 through 39, the range of motion further including an intermediate position between the proximal position and the distal position, the distal end of the dilation catheter engaging the enlarged tip of the guidewire at the intermediate position.

Example 41

The method of Example 40, the guidewire remaining stationary relative to the malleable shaft portion as the dilation catheter travels from the proximal position to the intermediate position.

Example 42

The method of any of Examples 40 through 41, the dilation catheter travelling proximally past the intermediate position during the act of driving the dilation catheter proximally.

Example 43

The method of Example 42, the guidewire traveling proximally with the dilation catheter as the dilation catheter travels from the distal position to the intermediate position.

Example 44

The method of Example 43, the proximal travel of the guidewire being arrested when the dilation catheter reaches the intermediate position, such that the guidewire no longer travels proximally with the dilation catheter as the dilation catheter continues to travel proximally from the intermediate position.

Example 45

The method of Example 44, the malleable shaft portion having a distal end, the distal end of the malleable shaft portion engaging the enlarged tip to arrest proximal travel of the guidewire when the dilation catheter reaches the inter-mediate position.

Example 46

The method of Example 45, the enlarged tip being posi-tioned at the distal end of the malleable shaft as the dilation catheter travels distally from the proximal position to the intermediate position.

Example 47

The method of any of Examples 44 through 46, the method further comprising coupling a first engagement feature of the dilation catheter with a second engagement feature of the guidewire, the coupling of the first engage-ment feature of the dilation catheter with the second engage-ment feature of the guidewire providing concomitant proximal translation of the dilation catheter and the guidewire as the dilation catheter travels from the distal position to the intermediate position.

Example 48

The method of Example 47, the malleable shaft portion having a distal end, the distal end of the malleable shaft portion engaging the enlarged tip and thereby decoupling the first engagement feature from the second engagement feature when the dilation catheter reaches the intermediate position.

Example 49

The method of any of Examples 38 through 48, the act of inserting further comprising positioning the malleable shaft portion in a Eustachian tube or in a passageway associated with drainage of a paranasal sinus.

Example 50

The method of Example 49, the act of inflating resulting in dilation of the Eustachian tube or passageway associated with drainage of a paranasal sinus.

Example 51

The method of any of Examples 37 through 50, the shaft assembly further including a position sensor, the method further comprising tracking the real-time position of the distal portion of the shaft assembly within the patient, based at least in part on signals from the position sensor.

Example 52

The method of Example 51, the position sensor being positioned within the enlarged tip.

Example 53

The method of any of Examples 37 through 52, the shaft assembly further including an illuminating element, the method further comprising confirming a position of the distal portion of the shaft assembly within the patient, based at least in part on a transillumination effect provided by the illuminating element.

Example 54

The method of Example 53, the illuminating element being positioned within the enlarged tip.

Example 55

The method of any of Examples 37 through 54, the act of driving the dilation catheter proximally comprising driving the dilation catheter back to the proximal position.

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Some versions of the examples described herein may be implemented using a processor, which may be part of a computer system and communicate with a number of peripheral devices via bus subsystem. Versions of the examples described herein that are implemented using a computer system may be implemented using a general-purpose computer that is programmed to perform the methods described herein. Alternatively, versions of the examples described herein that are implemented using a computer system may be implemented using a specific-purpose computer that is constructed with hardware arranged to perform the methods described herein. Versions of the examples described herein may also be implemented using a combination of at least one general-purpose computer and at least one specific-purpose computer.

In versions implemented using a computer system, each processor may include a central processing unit (CPU) of a computer system, a microprocessor, an application-specific integrated circuit (ASIC), other kinds of hardware components, and combinations thereof. A computer system may include more than one type of processor. The peripheral devices of a computer system may include a storage subsystem including, for example, memory devices and a file storage subsystem, user interface input devices, user interface output devices, and a network interface subsystem. The input and output devices may allow user interaction with the computer system. The network interface subsystem may provide an interface to outside networks, including an interface to corresponding interface devices in other computer systems. User interface input devices may include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

In versions implemented using a computer system, a user interface output device may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide a non-visual display such as audio output devices. In general, use of the term "output device" is intended to include all possible types of devices and ways to output information from computer system to the user or to another machine or computer system.

In versions implemented using a computer system, a storage subsystem may store programming and data constructs that provide the functionality of some or all of the modules and methods described herein. These software modules may be generally executed by the processor of the computer system alone or in combination with other processors. Memory used in the storage subsystem may include a number of memories including a main random-access memory (RAM) for storage of instructions and data during program execution and a read only memory (ROM) in which fixed instructions are stored. A file storage subsystem may provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem in the storage subsystem, or in other machines accessible by the processor.

In versions implemented using a computer system, the computer system itself may be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the example of the computer system described herein is intended only as a specific example for purposes of illustrating the technology disclosed. Many other configurations of a computer system are possible having more or fewer components than the computer system described herein.

As an article of manufacture, rather than a method, a non-transitory computer readable medium (CRM) may be loaded with program instructions executable by a processor. The program instructions when executed, implement one or more of the computer-implemented methods described above. Alternatively, the program instructions may be loaded on a non-transitory CRM and, when combined with appropriate hardware, become a component of one or more of the computer-implemented systems that practice the methods disclosed.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
(a) a body; and
(b) a shaft assembly extending distally from the body, the shaft assembly including;
  (i) a malleable distal portion having a distal end,
  (ii) an enlarged tip positioned at the distal end of the malleable distal portion,
  (iii) a position sensor positioned within the enlarged tip, the position sensor being configured to generate a signal indicating a position of the enlarged tip in three-dimensional space,
  (iv) an illuminating element positioned within the enlarged tip, the illuminating element being configured to emit light,
  (v) an inflatable balloon positioned proximal to the enlarged tip, the inflatable balloon being configured to dilate a passageway in an ear, nose, or throat of a patient, and
  (vi) a guidewire having a distal end, the enlarged tip being fixedly secured at the distal end of the guidewire.

2. The apparatus of claim 1, the shaft assembly further comprising a rigid proximal portion, the rigid proximal portion being positioned proximally in relation to the malleable distal portion.

3. The apparatus of claim 1, the enlarged tip having a ball shape.

4. The apparatus of claim 1, the malleable distal portion defining a lumen, the guidewire being positioned in the lumen.

5. The apparatus of claim 4, the enlarged tip defining an opening.

6. The apparatus of claim 5, the guidewire being translatable along the lumen and through the opening.

7. The apparatus of claim 6, further comprising a first slider, the first slider being translatable along the body to drive translation of the guidewire along the lumen and through the opening.

8. The apparatus of claim 7, the shaft assembly further comprising a dilation catheter, the dilation catheter being slidably positioned about the malleable distal portion, the dilation catheter including the inflatable balloon;

the apparatus further comprising a second slider, the second slider being translatable along the body to drive translation of the dilation catheter along the malleable distal portion.

9. The apparatus of claim 1, the guidewire having a distal end, the position sensor being positioned within the distal end of the guidewire, the distal end of the guidewire being positioned at the enlarged tip.

10. The apparatus of claim 1, the guidewire having a distal end, the illuminating element being positioned within the distal end of the guidewire, the distal end of the guidewire being positioned at the enlarged tip.

11. The apparatus of claim 1, the shaft assembly further comprising a dilation catheter, the dilation catheter being slidably positioned about the malleable distal portion, the dilation catheter including the inflatable balloon;

the apparatus further comprising a slider, the slider being translatable along the body to drive translation of the dilation catheter along the malleable distal portion.

12. The apparatus of claim 11, the malleable distal portion defining a lumen, the guidewire being slidably positioned in the lumen, the dilation catheter having a distal end configured to engage the enlarged tip to thereby drive distal translation of the guidewire and the enlarged tip relative to the malleable distal portion as the dilation catheter translates distally relative to the malleable distal portion.

13. The apparatus of claim 12, the dilation catheter further including a first engagement feature, one or both of the guidewire or the enlarged tip including a second engagement feature, the first and second engagement features being configured to couple with each other to thereby cause the dilation catheter to drive proximal translation of the guidewire and the enlarged tip relative to the malleable distal portion as the dilation catheter translates proximal relative to the malleable distal portion.

14. An apparatus comprising:
(a) a body;
(b) a shaft assembly extending distally from the body, the shaft assembly including;
   (i) a malleable distal portion having a distal end,
   (ii) a guidewire slidably disposed within the malleable distal portion, the guidewire including:
      (A) an enlarged tip, and
      (B) a position sensor positioned within the enlarged tip, the position sensor being configured to generate a signal indicating a position of the enlarged tip in three-dimensional space,
   (iii) a dilation catheter slidably positioned about the malleable distal portion, the dilation catheter having a distal end and an inflatable balloon positioned proximal to the distal end of the dilation catheter, the inflatable balloon being configured to dilate a passageway in an ear, nose, or throat of a patient; and
(c) an actuator, the actuator being operable to drive translation of the dilation catheter along the malleable distal portion;
   the distal end of the dilation catheter being configured to engage the enlarged tip to thereby drive distal translation of the guidewire and the enlarged tip relative to the malleable distal portion as the dilation catheter translates distally relative to the malleable distal portion.

15. The apparatus of claim 14, the dilation catheter being translatable between a proximal position and a distal position, the distal end of the dilation catheter being proximal to the distal end of the malleable distal portion when the dilation catheter is in the proximal position, the distal end of the dilation catheter being distal to the distal end of the malleable distal portion when the dilation catheter is in the distal position.

16. The apparatus of claim 15, the distal end of the malleable distal portion being configured to cooperate to position the enlarged tip at the distal end of the malleable distal portion when the dilation catheter is in the proximal position.

17. The apparatus of claim 16, the distal end of the malleable distal portion being configured to cooperate to decouple the first and second engagement features from each other as the dilation catheter travels from the distal position to the proximal position.

18. A method comprising:
(a) inserting a distal portion of a shaft assembly into an ear, nose, or throat of a patient, the shaft assembly including a dilation catheter, a malleable shaft portion, and a guidewire, the dilation catheter being slidably positioned about the malleable shaft portion, the dilation catheter including a balloon, the guidewire being slidably disposed in the malleable shaft portion, the guidewire having an enlarged tip;
(b) driving the dilation catheter distally in relation to the malleable shaft portion through a range of motion, the range of motion being from a proximal position to a distal position, a distal end of the dilation catheter engaging the enlarged tip of the guidewire as the dilation catheter translates distally from the proximal position to the distal position, the distal end of the dilation catheter driving the guidewire distally via the enlarged tip as the dilation catheter advances distally to the distal position;
(c) inflating the balloon of the dilation catheter while the dilation catheter is at the distal position; and
(d) driving the dilation catheter proximally in relation to the malleable shaft portion from the distal position.

* * * * *